US 9,006,173 B2

(12) United States Patent
Monks et al.

(10) Patent No.: US 9,006,173 B2
(45) Date of Patent: Apr. 14, 2015

(54) MICROCYSTINS AS AGENTS FOR TREATMENT OF CANCER

(75) Inventors: Noel R. Monks, Wilmore, KY (US); Shuqian Liu, Lexington, KY (US); Jeffrey A. Moscow, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 195 days.

(21) Appl. No.: 11/798,167

(22) Filed: May 10, 2007

(65) Prior Publication Data

US 2007/0275885 A1    Nov. 29, 2007

Related U.S. Application Data

(60) Provisional application No. 60/799,013, filed on May 10, 2006.

(51) Int. Cl.
| C07K 7/50 | (2006.01) |
| G01N 33/50 | (2006.01) |
| A61K 38/08 | (2006.01) |
| G01N 33/574 | (2006.01) |
| A61K 38/00 | (2006.01) |

(52) U.S. Cl.
CPC ........ *G01N 33/5011* (2013.01); *G01N 33/5014* (2013.01); *A61K 38/08* (2013.01); *G01N 33/574* (2013.01)

(58) Field of Classification Search
CPC ...................................................... A61K 38/12
See application file for complete search history.

(56) References Cited

U.S. PATENT DOCUMENTS

| 6,309,820 B1 * | 10/2001 | Sparks et al. ..................... 506/9 |
| 6,740,521 B2 * | 5/2004 | Isoda et al. ..................... 435/325 |
| 7,211,588 B2 * | 5/2007 | Gerlach et ..................... 514/314 |
| 7,601,494 B2 * | 10/2009 | Tian et al. ..................... 435/6.16 |
| 2007/0238667 A1 * | 10/2007 | Jia et al. ..................... 514/13 |
| 2007/0269531 A1 * | 11/2007 | Wolfe et al. ..................... 424/649 |
| 2009/0017452 A1 * | 1/2009 | Ratain et al. ..................... 435/6 |

OTHER PUBLICATIONS

OHSU Health (2008, updated) "Cancer information", http://www.ohsucancer.com/index.asp?fuseaction=cancerbyType.lookup&list=lung, pp. 1-6.*
Gehringer et al. (2005) Comparison of the structure of key variants of microcystin to vasopressin, Environ. Toxicol. Pharmacol., vol. 19, pp. 297-303.*
Islam et al. (2002) Synergistic cytotoxic effect between serine-threonine phosphatase inhibitors and 5-fluorouracil: a novel concept for modulation of cytotoxic effect, Cancer Chemother Pharmacol, vol. 49, No. 2, pp. 111-118.*
Wikipedia (2009, updated) Gastrointestinal cancer, http://en.wikipedia.org/wiki/Gastrointestinal_cancer, p. 1.*
Pyo et al. (2005) Trace analysis of microcystins in water using enzyme-linked immunosorbent assay, Microchem. J., vol. 80, No. 2, pp. 165-169.*
Monks et al. (2007) Potent cytotoxicity of the phosphatase inhibitor microcystin LR and microcystin analogues in OATP1B1- and OATP1B3-expressing HeLa cells, Mol. Cancer Ther., vol. 6, No. 2, pp. 587-598.*
Vécsey-Semjén et al. (2002) Novel colon cancer cell lines leading to better understanding of the diversity of respective primary cancers, Oncogene, vol. 21, pp. 4646-4662.*
Humpage et al. (1999) Microcystin-LR and liver tumor promotion : Effects on cytokinesis, ploidy, and apoptosis in cultured hepatocytes, Environ. Toxicol., vol. 14, pp. 61-75.*
Reference "Microcystins" (2009) Ecotoxicology Program, Integrated Risk Assessment Branch, Office of Environmental Health Hazard Assessment, California Environmental Protection Agency, pp. 1-21.*
der Pharmazie M. (2010) Expression of Organic Anion Transporting Polypeptides (OATPs) in Cancer Cell Lines and Tissues, Thesis of University Wien, pp. 1-59.*
ResearchCrossroads (2011) Microcystin Effects on Cell Cycle Events, /www.researchcrossroads.org/index.php?option=com_content&view=article&id=50%3Agrant-details&Itemid=37&grant_id=2545381, pp. 1-2.*
Rajesh et al. (1999) Ras Mutation, Irrespective of Cell Type and p53 Status, Determines a Cell's Destiny to Undergo Apoptosis by Okadaic Acid, an Inhibitor of Protein Phosphatase 1 and 2A, Am. Soc. Pharmcol. Exp. Therap., vol. 56, pp. 515-525.*
Lockhart et al. (2008) Organic anion transporting polypeptide 1B3 (OATP1B3) is overexpressed in colorectal tumors and is a predictor of clinical outcome, Clin. Exp. Gastroenterol., vol. 1, pp. 1-7.*
Reference "New Cancer Mentality: Dr. Arnold Glazier" (2011) pp. 1-23.*
Lee et al. (2008) Overexpression of OATP1B3 confers apoptotic resistance in colon cancer, Cancer Res., vol. 68, No. 24, pp. 10315-10323.*
Kurmayer et al. (2005) Genetic identification of microcystin ecotypes in toxic cyanobacteria of the genus *Planktothrix*, Microbiology, vol. 151, pp. 1525-1533.*
Zhu et al. (20050 Transformation of immortalized colorectal crypt cells by microcystin involving constitutive activation of Akt and MAPK cascade, Carcinogenesis, vol. 26, pp. 1207-1214.*
Damjana et al. (2011) Microcystins—potential risk factors in carcinogenesis of primary liver cancer in Serbia, vol. 15, issue 3, pp. 70-80.*
Steeg et al. (2012) Influence of human OATP1B1, OATP1B3, and OATP1A2 on the pharmacokinetics of methotrexate and paclitaxel in humanized transgenic mice, Clin. Cancer Res. 1-12.*
Cui et al., "Detection of the Human Organic Anion Transports SLC21A6 (OPT2) and SLC21A8 (OATP8) in Liver and Hepatocellular Carcinoma", Laboratory Investigation, vol. 83, No. 4, pp. 527-538, Apr. 2003.
Abe et al., "LST-2 A Human Liver-Specific Organic Anion Transporter, Determines Methotrexate Sensitivity in Gastrointestinal Cancers", Gastroentergology 2001, vol. 120, pp. 1689-1699, Jun. 2001.

(Continued)

*Primary Examiner* — Manjunath Rao
*Assistant Examiner* — Samuel Liu
(74) *Attorney, Agent, or Firm* — Crowell & Moring LLP

(57) ABSTRACT

This invention relates to the use of microcystins as agents for treatment of cancer. Also provided are methods of screening for microcystins with improved cytotoxicity.

18 Claims, 8 Drawing Sheets

(56) References Cited

OTHER PUBLICATIONS

Mackintosh et al., "Cyanobacterial microcystin-LR is a potent and specific inhibitor of protein phosphatases 1 and 2A from both mammals and higher plants", FEBS 08427, vol. 264, No. 2, pp. 187-192, May 1990.

Hagenbuch et al., "Organic anion transporting polypeptides of the OATP/SLC21 superfamily, new nomenclature and molecular/functional properties", Pflugers Arch—Eur J Physiol, vol. 447, pp. 653-665, 2004.

Monks et al., "Potent cytotoxicity of the phosphatase inhibitor microcystin LR and microcystin analogues in OARP1S1- and OATP1B3-expressing HeLa cells", Mol Cancer Ther, vol. 6, No. 2, pp. 587-598, Feb. 2007.

Tomoji Maeda et al., Uptake transporter organic anion transporting polypeptide 1B3 contributes to the growth of estrogen-dependent breast cancer, Journal or Steroid Biochemistry & Molecular Biology 122, (2010) 180-185.

Wooin Lee et al., Overexpression of OATP163 Confers Apoptotic Resistance in Colon Cancer, Cancer Res. 2008; 68 (24), Dec. 15, 2008.

Masato Narita et al., Expression of OATP1B3 determines update of Gd-EOb-DTPA in hepatocellular carcinoma; J. Gastroenterol (2009) 44: 793-798.

Abigail Daily et al., Abrogation of microcystin cytotoxicity by MAP kinase inhibitors and N-acetyl cysteine is confounded by OATP1B1 update activity inhibition, Toxicon 55 (2010) 827-837.

* cited by examiner

MICROCYSTINS AS AGENTS FOR TREATMENT OF CANCER

CONTINUING APPLICATION DATA

This application claims benefit of U.S. Provisional Application No. 60/799,013, filed May 10, 2006, which is incorporated by reference herein in its entirety.

FIELD OF THE INVENTION

This invention relates to the use of microcystins as agents for treatment of cancer. Also provided are methods of screening for microcystins with improved cytotoxicity.

BACKGROUND

Phosphorylation of intracellular proteins is a key mechanism in the regulation of signal transduction. Kinases, enzymes that catalyze protein phosphorylation, are mediators of the signal cascades, which activate multiple pathways involving the governance of cell division and cell death. Phosphatases are enzymes that counter the activity of kinases and remove organic phosphates from their active sites on regulatory molecules, which generally cause cessation of the activation signals. The importance of protein phosphatases in cell biology is underscored by the estimation that these proteins constitute greater than 1% of all of the proteins encoded in the human genome (1). Mammalian protein phosphatases have been placed into five subfamilies, designated PP1, PP2A, PP2B, PP5 and PP7 [reviewed in (2)].

Microcystins are inhibitors of PP1 and PP2A and are generally known as hepatotoxins that result from cyanobacterial contamination of water supplies. Structurally, microcystins are cyclic heptapeptides with the basic structure cyclo (D-Ala L-X-erythro-b-methyl-D-iso-ASP-L-Y-adda-D-iso-Glu-N-methyldehydro-Ala) where L-X and L-Y represent variable L-amino acids, and Adda is the b-amino acid 3-amino-9-methoxy-2,6,8-trimethyl-10-phenyldeca-4,6-dienoic acid (3). The most commonly studied microcystin is microcystin LR (FIG. 6), in which the two variable amino acids are leucine and arginine. The structures of at least 50 microcystin variants have been determined (4) differing almost exclusively in the two variable residues, which can be other L-amino acids in substitution for leucine and arginine. The variable nature of these compounds suggests that they may have a spectrum of biological effects and that there are opportunities for combinatorial engineering of therapeutic microcystin compounds.

The specific hepatic toxicity of microcystins results from the restricted hepatic expression of the organic anion transporters OATP1B1, OATP1B3 and OATP1A2, which mediate the cellular uptake of microcystins. OATP1B1 and OATP1B3 transporters have previously been known as Liver Specific Transporters 1 and 2 (LST1 and LST2), respectively, in recognition of gene expression limited to the liver. The potential potency of microcystin toxins in cancer cells has been difficult to examine due to the absence of expression of these transporters in most cancer cell lines. However, there is evidence for the expression of these transporters in tumors. Western blot analyses have detected the expression of both OATP1B1 and OATP1B3 in hepatocellular carcinoma (5, 6). Also, Abe et al. (7) have reported that OATP1B1 and OATP1B3 are expressed in a few cell lines created from liver, colon, and pancreatic tumors, suggesting that there may be a wider distribution of transporter gene expression in tumors than in normal tissues.

SUMMARY OF THE INVENTION

The present invention provides new methods for treating cancers, including treating tumors and/or metastatic disease and/or inhibiting the growth of tumors. The methods and combination therapies are preferably directed towards the treatment of OAT1B1- and/or OAT1B3-expressing cancers such as lung cancers, breast cancer, colon cancer, hepatocellular carcinoma and other tumors.

Accordingly, one aspect of the invention provides a method for treating cancer comprising administering to a subject in need thereof a pharmaceutically effective amount of a microcystin. Non-limiting examples of cancers to be treated are hepatocellular cancer, gastrointestinal cancer, lung cancer, gastric cancer, colon cancer, pancreatic cancer, gall bladder cancer, breast cancer, glioblastoma, and metastatic cancers and intraperitoneal disseminations thereof. The cancer is preferably hepatocellular cancer, gastrointestinal cancer, or non-small cell lung cancer. The microcystin can be a heptapeptide with the basic structure cyclo (D-Ala-X-erythro-β-methyl-D-iso-Asp-Y-Adda-D-iso-Glu-N-methyldehydro-Ala), where X and Y represent variable amino acids, and Adda is the β-amino acid, 3-amino-9-methoxy-2,6,8-trimethyl-10-phenyldeca-4,6-dienoic acid. Preferably, X and Y are L amino acids. More preferably, X is leucine and Y is either arginine, phenylalanine, or tryptophan.

Another aspect of the invention contemplates a combination therapy wherein a microcystin is used in combination with other cancer treatment modalities as known in the art.

The present invention also provides a method of screening for a microcystin with improved cytotoxicity, using cells transfected with at least one of OATP1B1 and OATP1B3. Preferably, the cells are transfected with OATP1B3.

DETAILED DESCRIPTION OF THE INVENTION

Figure 1:
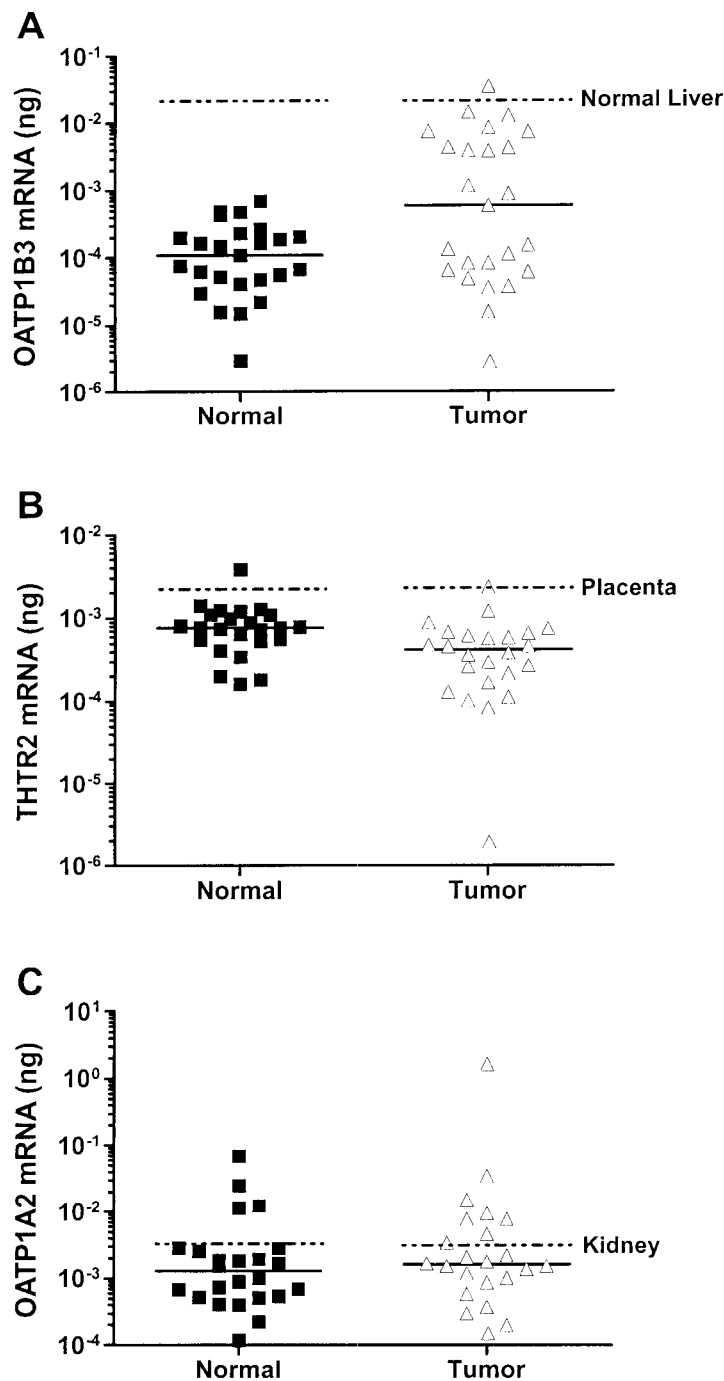
FIG. 1. Scatter plots displaying the expression levels of OATP1B3 (A), THTR2 (B) and OATP1A2 (C) for each of the 19 individual lung tumors (▲) and normal tissue (■) pairs. The solid line shows the median of the data set, whilst the dotted lines display the expression level in a reference sample from a normal tissue known to express the gene of interest. The data presented are expression level of each individual sample following normalization to β-actin.
Figure 2:
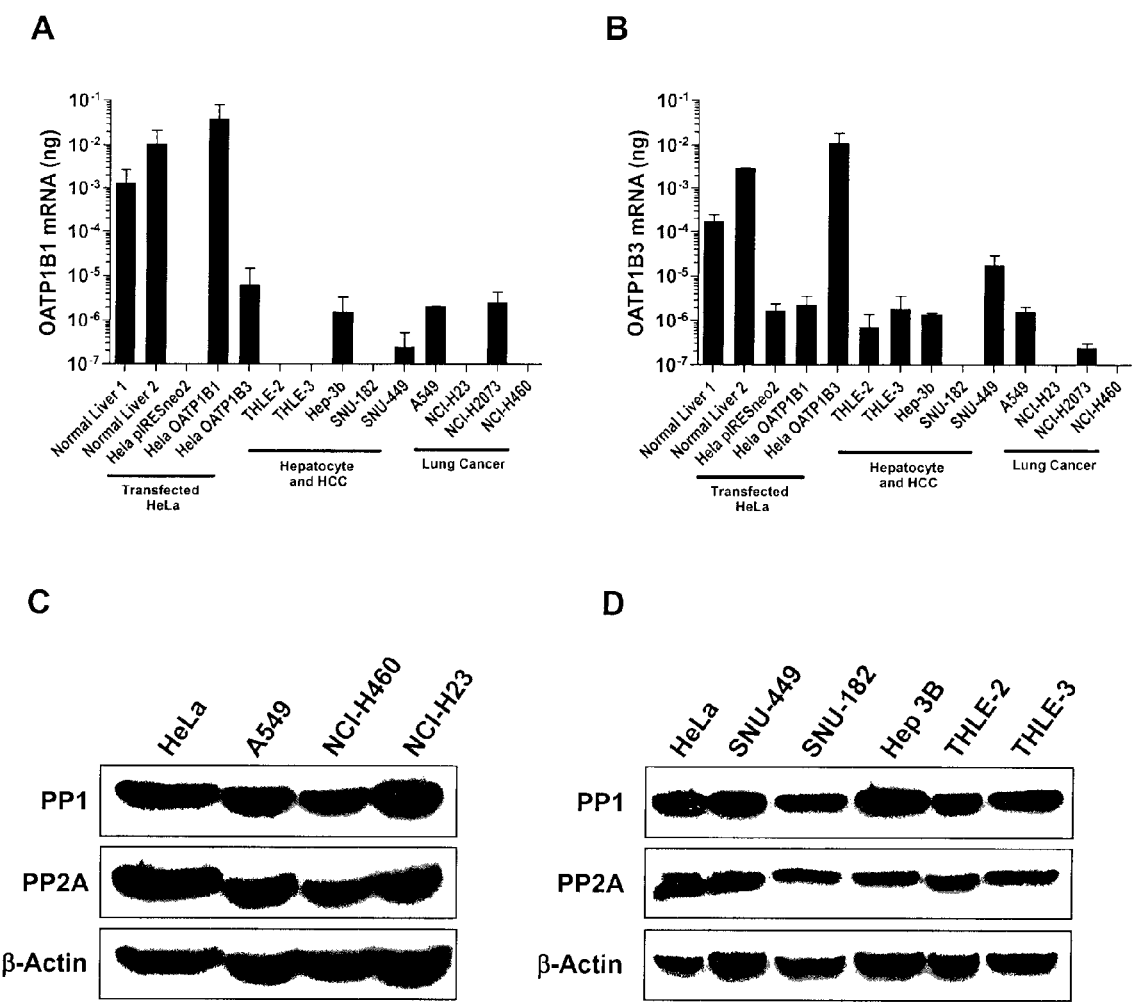
FIGS. 2A-2B. Expression levels of OATP1B1 and OATP1B3 in normal liver, transfected HeLa cells, immortalized hepatocyte cell lines, hepatocellular carcinoma cells (HCC), and lung cancer cell lines. Cells were collected and DNase treated RNA isolated as described in the Materials and Methods. Following cDNA synthesis, expression levels of OATP1B1 (A) and OATP1B3 (B) were analyzed using quantitative real-time PCR; β-actin levels were used to normalize the expression. The data presented are the Mean±SD of duplicate analysis. Protein phosphatases PP1 and PP2A are ubiquitously expressed in all of the cell lines. Whole cell lysates of Lung cancer (C) Hepatocellular carcinoma (D) cell lines, with HeLa cells used as a reference, were taken and equal amounts (25 μg/lane) of total protein were separated on a 10% SDS-PAGE gel, transferred to Nitrocellulose and immunoblotted for both PP1 and PP2A as described in the Materials and Methods. β-actin was used to demonstrate equal loading.

Our interest in microcystins as potential therapeutic molecules began with our finding that OATP1B3 mRNA is up-regulated in non-small cell lung cancer (NSCLC). Therefore, the anticancer potential of microcystin compounds might be exploited by targeting these compounds to tumors that are known to express OATP1B1 and OATP1B3.

Given that the microcystins are potent protein phosphatase inhibitors, they are likely to affect both cell cycling and apoptosis. PP1 and PP2A directly regulate the activity of proteins phosphorylated on serine or threonine residues. PP2A has been shown to regulate the activity of at least 50 protein kinases involved in critical aspects of the regulation of cell division and cell death, including PKC, Akt, ERK, MEK, IκB kinase, p38 and caspase-3 (8-10). Inhibition of PP2A (by okadaic acid) has been shown to increase the phosphorylation and subsequent activation of p53 leading to cell cycle arrest and apoptosis (11, 12). Recent studies have identified PP2A as a key regulator of BCL-2 (13). Pharmacological inhibition or RNAi knockdown of PP2A caused proteasomic degradation of phosphoryated BCL-2 and sensitized the cells to various cell death stimuli. Therefore, we hypothesized that tumor cells might be selectively sensitive to microcystin-induced phosphatase inhibition. To test this hypothesis we transfected cancer cells with the drug transporters OATP1B1 and OATP1B3 to create in vitro models in which microcystins could gain intracellular access, and the potential cytotoxicity of microcystins in cancer cells could be assessed.

As used herein, the term "cancer" is meant to include tumors, such as primary tumors that are the original neoplasm. The term "cancer" is also meant to include metastatic disease, metastases, and metastatic lesions, which are groups of cells that have migrated to a site distant relative to the primary tumor.

The term "cancer" embraces a collection of malignancies with each cancer of each organ consisting of numerous subsets. Typically, at the time of cancer diagnosis, the "cancer" consists in fact of multiple subpopulations of cells with diverse genetic, biochemical, immunologic, and biologic characteristics.

Preferably, the cancer is malignant.

The types of cancers to be treated by the methods of the instant invention are those that exhibit at least one of the organic anion transporters OATP1B1 and OATP1B3. Preferably, the cancers exhibit OATP1B3.

Preferred cancers include but are not limited to hepatocellular cancer, gastrointestinal cancer, lung cancer, gastric cancer, colon cancer, pancreatic cancer, gall bladder cancer, breast cancer, glioblastoma, and metastatic cancers and intraperitoneal disseminations thereof. The hepatocellular cancer can be hepatocellular carcinoma. The gastric cancer can be signet ring cell cancer of the stomach, signet ring carcinoma, or rubular adenocarcinoma. More preferred cancers are hepatocellular cancer, gastrointestinal cancer, and non-small cell lung cancer.

The microcystin can be a substrate of and thus target one or both of the organic anionic transporters OATP1B1 and OATP1B3. Preferably, the microcystin is a substrate of OATP1B3.

The microcystins contemplated for use in treating the above cancers may include compounds with the basic structure cyclo (D-Ala-X-erythro-β-methyl-D-iso-Asp-Y-Adda-D-iso-Glu-N-methyldehydro-Ala), where X and Y represent variable amino acids, and Adda is the β-amino acid, 3-amino-9-methoxy-2,6,8-trimethyl-10-phenyldeca-4,6-dienoic acid. Preferably, X and Y are L amino acids.

The microcystins can be naturally-occurring. At least fifty naturally-occurring microcystin analogs are known (WHO, Geneva: World Health Organization 1998:95-110). A preferred naturally-occurring microcystin is microcystin LR (FIG. 5), in which X is leucine and Y is arginine. Naturally-occurring microcystins can be isolated from natural sources, or can be synthetic structural equivalents of microcystins that can be isolated from natural sources.

The present invention also contemplates the use of novel synthetic microcystins for treatment of cancer. Novel synthetic microcystin analogs having beneficial biological effects can be designed using combinatorial engineering. A person of ordinary skill in the art will recognize that there are various methods applicable to microcystin synthesis, including solid phase peptide synthesis. Examples are described in the literature, including Aggen et al., Bioorg Med Chem 1999; 7:543-564; Gulledge et al., Bioorg Med Chem Lett 2003; 13:2903-2906; and Gulledge et al., Bioorg Med Chem Lett 2003; 13:2907-2911.

The present invention also contemplates the use of microcystins with improved cytotoxicity, i.e., microcystins having at least one of an improved cytotoxic potency or improved cytotoxic selectivity as compared to microcystin LR.

Microcystins with improved cytotoxic potency, or greater cytoxic potency than microcystin LR, demonstrate $IC_{50}$ values lower than the $IC_{50}$ values of microcystin LR in cells transfected with OATP1B1 and/or OATP1B3, with no significant increase in toxicity in control cells. Preferably, microcystins with improved cytotoxic potency demonstrate $IC_{50}$ values lower than the $IC_{50}$ values of microcystin LR in cells transfected with OATP1B3. Examples of microcystins with improved cytotoxic potency are microcystin LF and microcystin LW, as shown in the present Examples.

Microcystins with improved cytotoxic selectivity as compared to the selectivity of microcystin LR demonstrate an improved differential toxicity between cells transfected with OATP1B1 as compared to OATP1B3. Because the present invention contemplates treatment of cancers expressing OATP1B3 and not OATP1B1, cancers expressing OATP1B1 and not OATP1B3, and cancers expressing both transporters, a person of ordinary skill in the art will readily recognize that the definition of an "improved" differential toxicity will vary with the particular cancer to be treated. Preferably, microcystins with improved cytotoxic selectivity demonstrate an increased relative cytotoxicity in cells transfected with OATP1B3 as compared to cells transfected with OAT1B1. Examples of microcystins with increased relative cytotoxicity in cells transfected with OATP1B3 as compared to cells transfected with OAT1B1 are microcystin LF, microcystin LW, microcystin RR, and microcystin YR, as shown in the present Examples.

The present invention also contemplates microcystins with improved cytotoxicity with regard to the organic anion transporter OATP1A2, which is also known to mediate the cellular uptake of microcystins. For example, if the cancer exhibits OATP1B3, it may be beneficial to treat a patient with an improved microcystin analog that is a substrate for OATP1B3, but has reduced affinity (including no affinity) for OATP1A2 and/or OATP1B1.

Particularly referred microcystins with improved cytotoxicity are microcystin LF, in which X is leucine and Y is phenylalanine, and microcystin LW, in which X is leucine and Y is tryptophan.

The microcystins can be used alone, in combination with each other, or in combination with other cancer modalities, such as but not limited to chemotherapy, surgery, radiotherapy, hyperthermia, immunotherapy, hormone therapy, biologic therapy (e.g., immune effector mechanisms resulting in cell destruction, cytokines, immunotherapy, interferons, interleukin-2, cancer vaccine therapy, and adoptive therapy), and drugs to ameliorate the adverse side effects of such cancer modalities.

As described herein, microcystins form a family of structurally related cyclic peptides. An individual member of the microcystin family can be referred to variously herein as a "microcystin," a "microcystin analog," a "microcystin variant," or a "microcystin compound."

The terms "treating", "treatment", and the like are used herein to generally mean obtaining a desired pharmacological and physiological effect. More specifically, the reagents described herein which are used to treat a subject with cancer generally are provided in a therapeutically effective amount to achieve any one or more of the following: inhibited tumor growth, reduction in tumor mass, loss of metastatic lesions, inhibited development of new metastatic lesions after treatment has started, or reduction in tumor such that there is no detectable disease (as assessed by, e.g., radiologic imaging, biological fluid analysis, cytogenetics, fluorescence in situ hybridization, immunocytochemistry, colony assays, multiparameter flow cytometry, or polymerase chain reaction). The term "treatment", as used herein, covers any treatment of a disease in a mammal, particularly a human.

The term "subject" or "patient" as used herein is meant to include a mammal. Preferably the mammal is human.

The term "pharmaceutically effective" as used herein refers to the effectiveness of a particular treatment regime. Pharmaceutical efficacy can be measured based on such characteristics (but not limited to these) as inhibition of tumor growth, reduction of tumor mass, reduction of metastatic lesions as assessed, for example, by radiologic imaging, slowed tumor growth, lack of detectable tumor associated antigens, and the like. Additional methods of assessing tumor progression would be known to the treating and diagnosing physicians.

By "pharmaceutically effective amount" is meant an amount of an agent, reagent, compound, composition, or combination of reagents disclosed herein that when administered to a mammal is sufficient to be effective against the cancer.

The present invention contemplates the use of microcystins in combination with other cancer modalities or treatments.

Many treatments exist for cancers. The particular cancer therapy or combination of therapy modalities used to treat a cancer depend greatly on the type of cancer, its stage, the patient (e.g., weight, sex, age, health, prior cancers, and the like), and where the patient is in therapy (e.g., first treatment, in blast crisis, refractive to initial treatments, cancer relapse, or a second cancer perhaps induced by the treatment of the first cancer months or years before). Therefore, physicians will frequently have to combine a variety of treatment modalities that will best suit the needs of the patient in combating the disease and the patient's self-determination of quality of life. Treatment modalities include but are not limited to surgery, radiation therapy, chemotherapy, biologic therapy (e.g., cytokines, immunotherapy, and interferons), hormone therapies, and hyperthermia.

Conventional chemotherapy can be further broken down into hormone therapies (e.g., antiestrogens, aromatase inhibitors, gonadotropin-releasing hormone analogues, and anti-androgens), anti-tumor alkylating agents (e.g., mustards, nitrosoureas, tetrazines, and aziridines), cisplatin and its analogues, anti-metabolites (e.g., methotrexate, antifolates, 5-fluoropyrimidines, cytarabine, azacitidine, gemcitabine, 6-thipurines, and hydroxyurea), topoisomerase interactive agents, antimicrotubule agents (e.g., vinca alkaloids, taxanes, and estramustine), differentiating agents (e.g., retinoids, vitamin D3, polar-apolar compounds, butyrate and phenylactetate, cytotoxic drugs, cytokines, and combinations thereof), and other chemotherapeutic agents such as fludarabine, 2-chlorodeoxyadenosine, 2'-deoxycoformycin, homoharringtonine (HHT), suramin, bleomycin, and L-asparaginase.

Furthermore, the present invention contemplates delivery of the microcystins in combination with drugs (such as N-acetyl cysteine) that may selectively detoxify microcystins in hepatocytes but not in cancer cells, in order to decrease the hepatotoxicity of microcystin treatment.

The microcystins of interest discussed above preferably are administered as pharmaceutical compositions comprising pharmaceutically acceptable carriers, diluents, and/or excipients, which are vehicles commonly used to formulate pharmaceutical compositions for animal or human administration. The carriers, diluents and/or excipients are not intended to have biological activity themselves, and are selected so as not to affect the biological activity of the microcystins and any other active agent(s). A pharmaceutically acceptable carrier, diluent, and/or excipient as used herein includes both one and more than one such carrier, diluent, and/or excipient. Examples include but are not limited to distilled water, physiological phosphate-buffered saline, Ringer's solutions, dextrose solution, and Hank's solution.

Depending upon the manner of introduction, the microcystins may be formulated as, for example, sterile injectable formulations comprising aqueous solutions and/or suspensions containing the active materials in admixture with suitable carriers, diluents, and/or excipients. Formulations for oral use may be in the form of tablets or capsules.

The concentration of therapeutically active microcystins in the formulation (i.e., a formulation that is therapeutically effective to the subject to which it was administered) and the dose administered can be readily determined by a person of ordinary skill in the art. Typically, dosages used in vitro and in animal models may provide useful guidance in the amounts useful for in vivo administration. Preferably, the dose administered will be less than the hepatotoxic dose.

The microcystins may be administered locally or systemically in a therapeutically effective dose.

The methods of administration include but are not limited to parenteral administration, including subcutaneous (s.c.), subdural, intravenous (i.v.), intramuscular (i.m.), intrathecal, intraperitoneal (i.p.), intracerebral, intraarterial, intralesional, and pulmonary (e.g., via aerosols, inhalation, or powder) routes of administration. Administration can be via surgical application or surgical suppository. Oral administration is also contemplated.

According to one aspect of the invention, a microcystin may be administered alone, or in combination with other agents as discussed above to treat and/or ameliorate a cancer. Administration of other cancer therapeutic agents can occur prior to, concurrent with, or after administration with the microcystins. Administration of the microcystins can occur before, during or after surgical treatment, radiotherapy, hormone therapy, immunotherapy, hyperthermia, or other cancer treatment modality. Administration of the microcystins can occur daily, weekly, or monthly as needed.

One aspect of the invention contemplates a method of screening for microcystins with improved cytotoxicity.

Microcystins with improved toxicity are described above.

The present invention contemplates using cells transfected with at least one of OAT1B1 and OAT1B3 to determine the cytotoxicity of candidate microcystin analogs. In one aspect of the invention, transfected cells are treated with the microcystin, followed by determination of cell growth. In another aspect of the invention, phosphatase inhibition in the microcystin-treated cells is measured.

It must be noted that as used herein, the singular forms "a", "and", and "the" include plural referents unless the context clearly dictates otherwise. Thus, for example, reference to "a microcystin" or "microcystin analog" includes a plurality of such microcystins or microcystin analogs, and reference to "the dosage" includes reference to one or more dosages and equivalents thereof known to those skilled in the art, and so forth.

EXAMPLES

Abbreviations

OATP, Organic Anion Transporting Polypeptide; PP1, protein phosphatase-1; PP2A, protein phosphatase-2A; LST, Liver Specific Transporters; NSCLC, non-small cell lung cancer; PKC, Protein Kinase C; Akt, Protein Kinase B, ERK, extracellular signal-regulated kinases, MEK, MAPK kinase, IκB kinase, Inhibitor of κB kinase; DMEM, Dulbecco's Modified Eagles Medium; FBS, fetal bovine serum; DOC, Sodium deoxycholate; TBS, Tris buffered saline; CCK-8, Cholecystokinin Octapeptide; BSP, Bromosulfophthalein; SRB Sulforhodamine B; TCA, Trichloracetic Acid; DTT, dithiothreitol; MyBP, Myelin Basic Protein; JNK, c-Jun N-terminal kinase; NAC, N-acetylcysteine; BSO, buthionine sulfoximine; SSC, Side scatter: FSC, Forward scatter.

Materials and Methods

Reagents and Cell Culture.

HeLa cervical adenocarcinoma cells were obtained from the American Type Culture Collection (Manassas, Va.). Dulbecco's Modified Eagles Medium (DMEM) containing GLUTAMAX™-I, fetal bovine serum (FBS), phosphate buffered saline (PBS) pH 7.2 and LIPOFECTAMINE™ 2000 were purchased from Gibco (Carlsbad, Calif.). Lung tumor specimens and matched adjacent non-malignant tissue pairs were obtained from the NCI Cooperative Human Tissue Network (CHTN; Columbus, Ohio). Normal liver cDNA was purchased from Biochain Institute, Inc (Hayward, Calif.). Microcystins LR and YR were purchased from Sigma, (St Louis, Mo.). Microcystin LF, LW, RR and Okadaic acid were all purchased from Axxora, LLC (San Diego, Calif.). [$^{33}$P]-ATP was purchased from PerkinElmer (Boston, Mass.). All other chemicals were purchased from Sigma.

Transporter Gene Expression Analysis by Quantitative PCR.

A protocol to screen anonymous lung tumor specimens for transporter gene expression was approved by the University of Kentucky Institutional Review Board. For each transporter gene, we identified a primer set using the program Oligo 4.0. In each case we demonstrated that the primers amplify a PCR product of expected length. Total RNA was extracted from normal lung tissue and paired lung cancer specimens and cell lines using the RNEASY kit (QIAGEN) with an on-column DNase digestion. A total of 3 µg of RNA was used as a template for the first-strand cDNA synthesis using the THERMOSCRIPT™ RT-PCR system (Invitrogen, Carlsbad, Calif.) with Oligo(dT) as the primer and performed according to the manufacture's protocol. Quantitative real-time PCR was performed using the SYBR® Green PCR Kit (Applied Biosystems; Foster City, Calif.) and the iCycler thermal cycler (Bio-Rad). Quantification was performed using iCycler analysis software. The fluorescence threshold was set above the baseline in the exponential phase of the PCR and from this the Ct (threshold cycle) was calculated for each reaction. The number of cycles required to reach the threshold fluorescence is proportional to the amount target RNA in the sample. The relative expression levels of the target genes were determined by calculating the relative amounts of RNA from PCR standard curves (cDNA from liver, kidney or placenta was used as standards for the lung tissue expression analysis, plasmid DNA was used to for the cell line expression analysis), followed by normalization to the endogenous reference gene β-actin. All PCR products of the samples displayed a single, sharply melting curve with a narrow peak. Both OATP1B1 and OATP1B3 share >80% homology at the nucleotide level, therefore primer specificity was confirmed by the inclusion of a negative control to each analysis, (plasmid containing the alternative gene). Neither of the primer sets amplified the other gene.

Transient Expression of OATP1B1 and OATP1B3.

OATP1B1 and OATP1B3 cDNAs inserted into the multiple cloning site of the vector pIRESneo2 were obtained from Drs. Meier and Hagenbuch at the University of Zurich, and the nucleotide sequences of the coding regions were confirmed by nucleic acid sequencing.

Exponentially growing HeLa cells were seeded at $2 \times 10^5$ cells/well in 6-well plates in 2 ml of DMEM supplemented with 5% fetal calf serum (without antibiotics). The cells were transfected 24 hours later using LIPOFECTAMINE™ 2000 (Invitrogen) at a ratio of lipid:DNA of 2:1 (2 µl:1 µg). In short, 2 µl of LIPOFECTAMINE™ 2000 diluted into 200 µl of OPTI-MEM® (Invitrogen), at the same time 1 µg of plasmid DNA is also diluted into 200 µl of OPTI-MEM® and left to equilibrate for 5 minutes. The DNA and LIPOFECTAMINE™ 2000 dilutions were mixed by pipetting and complexes allowed to form for 25 minutes. During complex formation the cells were washed cells once with 37° C. PBS and 600 µl of DMEM supplemented with 5% fetal calf serum was added to each well. After 25 minutes, the complex mixture (400 µl) was carefully added to the cells, mixed gently, and the transfection allowed to proceed at 37° C., in 5% $CO_2$ for 4 hours. After 4 hours 1 ml of DMEM supplemented with 10% fetal calf serum was added to each well and the cells returned to the incubator.

Western Blot Analysis.

Cells were washed twice in ice-cold PBS, lysed without trypsinisation for 10 minutes at 4° C. using a lysis buffer containing 150 mM NaCl, 50 mM Tris.Cl, pH 8.0, 1% NP-40, 0.5% DOC, 0.1% SDS and 0.02% sodium azide and 80 µl/ml of Complete Protease Inhibitor cocktail (Roche Applied Science, Indianapolis, Ind.). Samples were passed through a 25-gauge needle 10 times, and the lysate collected following centrifugation at 12,000 g for 5 minutes at 4° C. Protein concentrations were determined using the Bio-Rad DC protein assay (Bio-Rad, Hercules, Calif.). Equal amount of protein (25 µg/lane) were separated by 10% SDS-polyacrylamide gel electrophoresis (PAGE) and subsequently transferred to PROTRAN BA85 nitrocellulose membrane (Whatman, Inc. Sanford Me.). The membranes were incubated with antibodies against PP1 and PP2A (Santa Cruz Biotechnology, Inc. Calif.) in 5% non-fat milk. After washing with TBS-Tween the membranes were incubated with peroxidase-conjugated goat anti-mouse or goat anti-rabbit antibody (Jackson Immunoresearch Laboratories, Inc., West Grove, Pa.) in 5% non-fat milk, followed by visualisation using the enhanced chemiluminescence system (Amersham Biosciences, Piscataway, N.J.). β-actin (Sigma) was used to confirm equal protein loading.

Drug Uptake Studies.

Exponentially growing HeLa cells were transiently transfected with the plasmids containing OATP1B1, OATP1B3 or empty pIRESneo2 as described above. 48 hours after transfection, the cells were exposed to two commercially available, radiolabeled substrates in uptake buffer (142 mM NaCl, 5 mM KCl, 1 mM $K_2HPO_4$, 1.2 mM $MgSO_4$, 1.5 mM $CaCl_2$, Glucose 5 mM and HEPES 12.5 mM—pH 7.3): [$^3$H]-BQ123 (Amersham Biosciences, N.J.) for 30 minutes (final concentration 0.5 µM), a substrate for both transporters (14) and [$^3$H]-CCK-8 (Cholecystokinin Octapeptide, Amersham Biosciences) for 10 minutes (5 nM), a substrate specific for the OATP1B3 transporter (14). The uptake assay was terminated by aspiration of the medium and three successive washes with ice-cold PBS. The cells were air dried and solubilized by overnight incubation in 0.2 N NaOH, followed by neutralization with 0.2 N HCl. The amount of intracellular radioactivity in the lysates was determined by liquid scintillation counting. The results were calculated by the subtraction of time-zero counts followed by normalization to the amount of cellular protein present in the lysates, which was determined spectrophotometrically using the Bio-Rad protein assay. Inhibition of transport was performed by coincubation with 50 µM bromosulfophthalein (Sigma).

Growth Inhibition Studies.

Cells were taken 24 hours following transfection and seeded into 96 well plates at $1 \times 10^4$ cells/ml ($1 \times 10^3$ cells/well) and allowed to adhere for a further 24 hours prior to drug treatments. The cells were then exposed to serial dilutions of the microcystin analogs prepared in culture medium for 72 hr. Experiments in which cells were exposed to microcystin LR for 1 and 6 hours, the media was carefully aspirated from the wells and replaced with 200 µl of fresh media. Cellular growth was determined using the sulforhodamine B (SRB) protein dye assay (15). In short, cells were fixed with 50% TCA w/v (50 µl/well) for 1 hour at 4° C. Following fixation, the plates were washed 5-6 times in water and stained with SRB (0.4% SRB (w/v) in 1% (v/v) acetic acid) for 30 minutes at 37° C. Excess stain was removed by washing 5 times in 1% (v/v) acetic acid. The plates were subsequently air-dried and the protein-bound SRB re-solubilized by the addition of 10 mM Trizma Base, pH 10.5. Colorimetric readings were made at 570 nm. The $IC_{50}$ was calculated from the dose response curve as the concentration of drug that produced a 50% decrease in the mean absorbance compared to the untreated wells.

Clonogenic Survival Studies.

HeLa cells were transiently transfected with OATP1B1, OATP1B3 or empty pIRESneo2 as described above. 48 hours after transfection, cells were seeded into 60 mm culture dishes at 200 cells/dish in 5 ml of media. 6 hours after seeding, microcystin LR was added to duplicate dishes and left for a further 72 hours. Following microcystin LR exposure, the media was careful aspirated from the dishes and replaced with 5 ml of fresh media. The dishes were left for approximately 7 days until colonies were visible, at which time the cells were washed once with PBS, fixed using Carnoy's Fixative (methanol:acetic acid—3:1) for 5 minutes and stained using 0.4% crystal violet dissolved in water. The number of colonies on each plate was counted by eye and survival calculated as the percentage of control. The $LC_{50}$ was extrapolated from the graph and is defined as the concentration at which the number of colonies was 50% of the control. The cloning efficiency is each transfected cell line was >95%.

Inhibition of Purified Protein Phosphatases.

Phosphatase activity was determined using the Protein Serine/Threonine Phosphatase (PSP) Assay System (New England BioLabs Inc. MA). The in vitro activity of purified PP1 (New England Biolabs) and PP2A (Upstate Cell Signaling Solutions, NY) was assayed according to the manufacturers instructions. Briefly, PP1 or PP2A were diluted in phosphatase assay buffer (50 mM Tris-HCl (pH 7.5), 0.1 mM $Na_2EDTA$, 5 mM DTT and 0.01% Brij 35) at a concentration were the enzyme concentration is linear with dephosphorylation (≈30%) of the [$^{33}$P]-ATP labeled Myelin Basic Protein (MyBP). The inhibitory effects of okadaic acid and the microcystin analogs, was determined by pre-incubation of the enzymes with serial dilutions of each compound for 10 minutes prior to the addition of the radiolabeled substrate. [$^{33}$P]-MyBP was added to the reaction (final reaction volume 50 µl) and immediately incubated at 30° C. for 10 minutes. The reaction was stopped by the addition of 200 µl of ice-cold 20% TCA and incubated for a further 10 minutes on ice. The precipitated protein was pelleted by centrifugation at 12,000 g at 4° C. for 5 minutes, following which 200 µl of the supernatant was carefully removed and the amount of released $^{33}$P determined by liquid scintillation counting. The data were normalized to a duplicate control reaction performed in the absence of the phosphatases. The $IC_{50}$ was calculated as the concentration of drug that inhibited the release of $^{33}$P compared to an uninhibited control reaction.

Intracellular Protein Phosphatase Analysis.

To determine the effects of the microcystins on the activity of the intracellular phosphatases in the transiently transfected HeLa cells, cell lysates were prepared as follows. 48 hours following transfection, HeLa cells transfected with either pIRESneo2, OATP1B1 or OATP1B3 were treated with microcystin analogs and okadaic acid at approximately $IC_{90}$ concentrations for 6 hours. The cells were subsequently washed in ice-cold PBS and 500 µl of the phosphatase assay buffer containing 80 µl/ml of Complete Protease Inhibitor cocktail was added to each well, the cells were immediately scraped, collected in 1.5 ml microcentrifuge tubes and freeze/thawed twice in dry-ice/room temperature water. The cells were further lysed by repeated pipetting (×10) and immediately centrifuged at 12,000 g for 10 minutes at 4° C. The remaining supernatant was collected and frozen at −80° C. The protein concentration of the cell lysates was measured using the Bio-Rad protein assay. To determine the levels of phosphatase inhibition in the microcystin treated cells, 20 ng of cellular protein was incubated in phosphatase assay buffer in the presence of [$^{33}$P]-ATP labeled MyBP as described above. The results are presented as the percent of total phosphatase activity relative to untransfected untreated HeLa cells.

Cellular and Nuclear Morphology Studies.

HeLa cells were transiently transfected with OATP1B1 or empty pIRESneo2 as described above. Forty eight hours after transfection, the cells were treated with 10 nM microcystin LR for 6 hours. Floating and adherent cells were subsequently pooled and washed once with ice cold PBS. Cells were then either fixed in Carnoy's fixative or live cells immediately analyzed by flow cytometry, (SSC—side scatter (granularity) versus FSC—forward scatter (relative size), to determined changes in gross cell morphology relative to a control (untreated) population. Flow cytometry was performed using a BD FACSCALIBUR™ system (BD Biosciences, NJ). Fixed cells were stained with Hoechst 33258 (1 µg/ml dissolved in PBS) and changes in nuclear/DNA morphology were determined by fluorescent con-focal microscopy. Brightfield and fluorescent images were taken under a 40× oil immersion objective using a confocal Leica DM IRBE inverted microscope equipped with a Spectra-Physics 2 photon sapphire/titanium laser and transmitted light detector for differential interference contrast and phase microscopy.

Results

Example 1

OATP1B3 Expression is Increased in NSCLC Tumors Relative to Adjacent Non-Malignant Tissue We analyzed the expression of 19 drug and vitamin transport genes in 19 pairs of NSCLC tumors and surrounding non-malignant tissue obtained from the NCI Cooperative Human Tissue Network. RNA extracted from tumors was analyzed for transporter gene expression using quantitative, real-time PCR and the results were normalized to the expression of β-actin. The ratio between the expression in tumor compared to adjacent non-malignant tissue for each paired sample was calculated and the median value for the series of tumor—tissue pairs for each gene is presented in Table 1.

TABLE 1

Ratio of transporter gene expression in lung tumors compared to normal surrounding tissue

| Transporter | Gene symbol | Tumor/Normal Ratio |
|---|---|---|
| OAT1 | SLC22A6 | 0.62 |
| OAT2 | SLC22A7 | 0.90 |
| OAT3 | SLC22A8 | 1.17 |
| OAT4 | SLC22A11 | 1.11 |
| OATP1A2 | SLC21A3 | 1.28 |
| OATP1B3 | SLC21A8 | 6.38 |
| OATP1C1 | SLC21A14 | 0.68 |
| OATP2A1 | SLC21A2 | 0.18 |
| OATP2B1 | SLC21A9 | 0.47 |
| OATP3A1 | SLC21A11 | 0.95 |
| OATP4A1 | SLC21A12 | 1.24 |
| OCT1 | SLC22A1 | 0.81 |
| OCT2 | SLC22A2 | 0.36 |
| OCT3 | SLC22A3 | 0.33 |
| OCTN1 | SLC22A4 | 0.25 |
| OCTN2 | SLC22A5 | 0.81 |
| RFC1 | SLC19A1 | 0.78 |
| THTR1 | SLC19A2 | 0.67 |
| THTR2 | SLC19A3 | 0.35 |

Table 1 shows relative expression levels of 19 drug and vitamin transport genes in 19 pairs of NSCLC tumors compared to surrounding non-malignant tissue, obtained from the NCI Cooperative Human Tissue Network. DNase treated mRNA was isolated from tissues as described in the Materials and Methods. Following cDNA synthesis, expression levels of each gene were analyzed using quantitative real-time PCR. β-actin levels were used to normalize the expression and data are presented as the ratio of the median tumor expression compared to the median of the paired normal tissue.

The mRNA of only one gene, OATP1B3 was found to be up-regulated, by a median value of 6.4-fold in lung tumors compared to surrounding normal tissue; whereas all of the other transport genes showed little increase in expression. A number of genes did show a decrease in lung tumor expression with the transporters OATP2A1, OCT2, OCT3, OCTN1 and THTR2 all showing >3-fold drop in expression. The decrease RNA levels of THTR2 in this series is consistent with our previous study of THTR2 RNA levels in NSCLC, which used a different set of NSCLC tumor/tissue pairs and a different methodology (hybridization of labeled probes to a cDNA array) (16), and which also found a decrease in THTR2 RNA levels in NSCLC tumors relative to adjacent non-malignant tissue.

To further illustrate the changes in expression between tumor and normal lung tissue, representative scatter plots for OATP1B1 (A), THTR2 (B) and OATP1A2 (C) are shown in FIG. 1. The solid line represents the median value presented in Table 1; the dotted line represents a reference sample showing the expression in a normal tissue known to express each gene. Of particular interest is the increased expression of OATP1B3 in a number of the lung tumor samples (FIG. 1A) which is comparable to the expression level of OATP1B3 in normal liver, Example 2

HeLa Transient Transfection Model Demonstrates Equivalent Levels of Transporter Expression to Liver and PP1 and PP2A Expression Suitable for the Study of Microcystins To explore whether OATP1B3 expression could confer sensitivity to its toxic substrates (e.g. microcystin), and thus be exploited as potential target in lung cancer, hepatic cancer and other malignancies, a transgenic model of OATP1B3 and the closed related gene OATP1B1 was needed. Because of their relative ease of transfection and capacity to express transgenes, we performed initial investigations in HeLa cells as a proof-of-principle. Exponentially growing HeLa cells were transiently transfected with the expression plasmids containing the OATP1B1 and OATP1B3 cDNA inserts, or a plasmid without a cDNA insert (vector control). To confirm the expression level of the cloned cDNAs and to determine the approximate level of expression in the transfected HeLa cells relative to both control cells and normal liver cDNA, we performed real-time-PCR as shown in FIG. 2 (panels A and B). These studies demonstrate that the RNA levels in the transient transfection system approximate the levels seen in normal adult liver. Of significant interest, we observed that the hepatic-derived cell lines have lost expression of these transporters in comparison to normal liver, and lung cancer cell lines also have either very low or undetectable levels of RNA expression of these transporter genes.

Since microcystins are known substrates of OATP1B1 and OATP1B3 and are also acknowledged inhibitors of PP1 and PP2A, it was important to demonstrate that HeLa, lung and hepatic cancer cells express PP1 and PP2A, Western blot analysis was performed using antibodies directed against PP1 and PP2A (FIG. 2, panels C and D). This study demonstrates that both phosphatases are present in HeLa cells, indicating that HeLa cells would make an appropriate in vitro model system. The studies also show that PP1 and PP2A are present in cell lines created from tumors that are known to express OATP1B1 and/or OATP1B3: the lung cancer cell lines A549, NCI-H460 and NCI-H23; and the hepatocellular carcinoma cell lines SNU-449, SNU-182 and HepB3. The SV40 immortalized hepatic cell lines THLE-2 and THLE-3 are also shown.

Example 3

HeLa Expression Models Exhibit Functional Activity and Confers Increased Sensitivity to Microcystin LR and Other Natural Microcystin Analogs To determine whether the RNA expression in transiently transfected HeLa cells resulted in functional activity of the transport genes, we studied the uptake of radiolabeled BQ123, a substrate for both OATP1B1 and OATP1B3 and CCK-8, a substrate specific for OATP1B3 only. As shown in FIG. 3, gene-specific uptake of BQ123 can be seen in both OATP1B1- and OATP1B3-transfected cells (panel A), and OATP1B3-specific uptake of CCK-8 can be seen in OATP1B3-transfected cells (panel B). In both cases, uptake activity was inhibited by an excess of BSP (50 μM), a known competitive inhibitor of these transporters. These studies demonstrate that the functional activity of the cloned, transfected genes is consistent with the previously reported substrate profile of these transporters (14). To determine whether the functional expression of OATP1B1 and OATP1B3 result in change sensitivity to microcystin LR, we exposed the transfected HeLa cells to microcystin LR in a 72 hour growth inhibition assay. As can be seen in FIG. 3C, the $IC_{50}$ for microcystin LR in OATP1B1 cells was 5±1 nM and the $IC_{50}$ for OATP1B3 cells was 39±8 nM, while the toxicity in the control cells was not reached at 10 μM. Similar results were seen using the clongenic assay (FIG. 3D), which again identified the differential sensitivity for microcystin LR between OATP1B1 ($LC_{50}$=2 nM) and OATP1B3 (($LC_{50}$=30 nM), with no toxicity seen in the vector alone (pIRESneo2) cells. These results demonstrate the potential selective toxicity that the expression of these transporter genes confer on HeLa cells after exposure to microcystin LR.

To determine whether microcystin toxicity can be specifically inhibited in OATP1B1 and OATP1B3-transfected cells, we performed a growth inhibition study with microcystin LR in the presence or absence of BSP. As can also be seen in FIG. 3C, BSP significantly shifted the growth inhibition curve to the right, increasing the $IC_{50}$ for both OATP1B1 and OATP1B3-transfected cells from 5 nM and 39 nM, respectively, to approximately 5 μM, further confirming the role of OATP1B1 and OATP1B3 uptake in microcystin LR toxicity. To further understand the activity of microcystin LR, we exposed OATP1B1-transfected HeLa cells to microcystin LR for 1, 6 and 72 hours (FIG. 3E). A 1 hour exposure was found to be less active, whilst the 6 hour exposure was similar to 72 hours, identical results were obtained with OATP1B3-transfected cells (data not shown). This result demonstrates that toxic effects of microcystin LR are rapid, reaching a maximum effect after only 6 hours of incubation.

We subsequently examined four other microcystin analogs using growth inhibition assays in the transfected HeLa cells to determine whether there was evidence that different structural analogs had greater potency or selectivity than microcystin LR. We also used okadaic acid, the classical phosphatase inhibitor that was not thought to have selective uptake requirements, as a positive control. As shown in Table 2, two of the analogs examined, microcystin LF and microcystin LW, showed greater cytotoxic potency than microcystin LR, with both demonstrating $IC_{50}$ values in both of the gene-transfected cell lines of less than 1 nM, with no evidence of toxicity in the vector-only transfected cells at concentrations up to 1 µM. Microcystin RR exhibited much less potent cytotoxicity, with an $IC_{50}$ of 3.8±2.3 µM and 0.58±0.40 µM for OATP1B1 and OATP1B3-transfected cells, respectively. Still, the transporter gene expression increased cytotoxicity of microcystin RR, with the vector-transfected cells not showing any cytotoxicity at concentrations up to 10 µM. Both microcystins LR and RR demonstrated differential toxicity between the cells transfected with the either OAPT1B1 and OATP1B3. This data demonstrates that structural variation in the microcystin analogs provides a degree of transporter selectivity.

Figure 4:
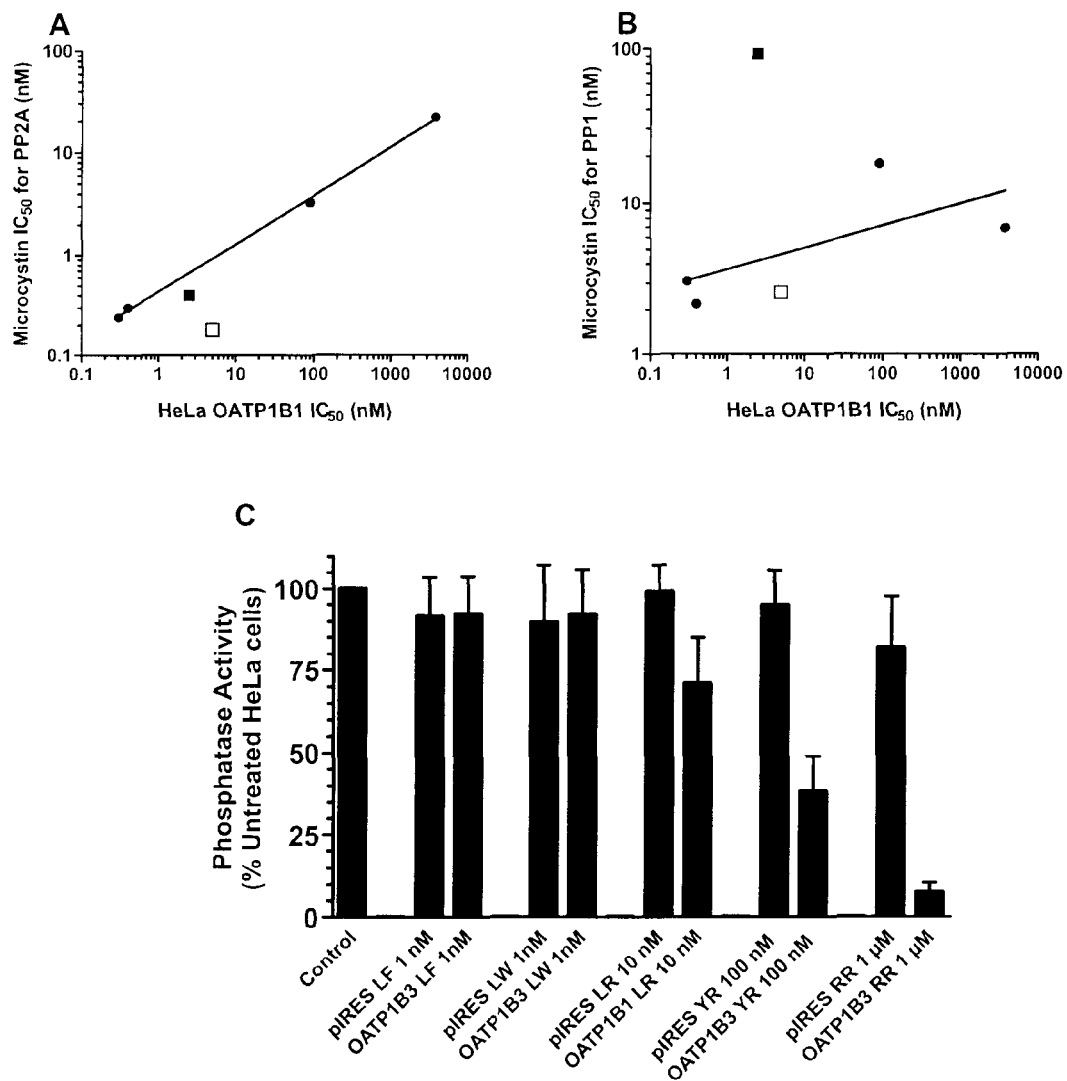
FIGS. 4A-4C. Correlations between growth inhibition and in vitro enzyme inhibition (data from Table 2). The relationship between the growth inhibition $IC_{50}$ for the microcystin analogs and the in vitro enzyme inhibition $IC_{50}$ of PP2A (A), and PP1 (B). The filled circles (●) represent the microcystin analogs LW, LF, RR, and YR. The open square (□) is microcystin LR, and the closed square (■) is okadaic acid. The Linear regression analysis was performed using the GRAPH-PAD PRISM® Software. Inhibition of total phosphatase activity in transfected HeLa cells exposed to equitoxic concentrations ($IC_{90}$) of the microcystin analogs (C). Intra-cellular phosphatase enzyme inhibition was determined using whole cell lysates prepared from transfected HeLa cells exposed to $IC_{90}$ concentrations of the Microcystin analogs for 6 hours as described in the Materials and Methods. 20 ng of cellular protein was incubated in phosphatase assay buffer in the presence of [$^{33}$P]-ATP labeled MyBP for 10 minutes, after which the reaction was stopped with TCA and released [$^{33}$P] was determined by liquid scintillation counting. The data are presented as the percent phosphatase activity relative to untransfected and untreated HeLa cells. All data are presented as the mean±SD. of 3 replicate experiments.

Further evidence for the importance of selective phosphatase inhibition in cytotoxicity is provided in FIG. 4, which shows the correlation between the data in Table 2. FIGS. 4A and 4B show the relationship between the growth inhibition $IC_{50}$ for the microcystin analogs and the in vitro enzyme inhibition $IC_{50}$ of PP2A and PP1, respectively, where microcystin LR is represented by the open square (excluded from the linear regression analysis). In FIG. 4A, the near linear relationship between HeLa growth inhibition and PP2A enzyme inhibition ($r^2>0.99$) of 4 microcystin analogs (filled squares) suggests that the activity of these analogs in the

TABLE 2

Microcystin analog growth inhibition and protein phosphatase enzyme inhibition

| | Growth Inhibition | | | Enzyme Inhibition | |
|---|---|---|---|---|---|
| Microcystin analog | pIRESneo2 $IC_{50}$ (nM) | OATP1B1 $IC_{50}$ (nM) | OATP1B3 $IC_{50}$ (nM) | PP1 $IC_{50}$ (nM) | PP2A $IC_{50}$ (nM) |
| LR | >10,000 | 5 ± 51 | 39 ± 8 | 1.4 ± 0.3 | 0.18 ± 0.01 |
| LF | >1000 | 0.4 ± 0.1 | 0.9 ± 0.9 | 2.2 ± 1.5 | 0.30 ± 0.01 |
| LW | >1000 | 0.3 ± 0.1 | 0.5 ± 0.4 | 3.1 ± 0.3 | 0.24 ± 0.02 |
| RR | >10,000 | 3,800 ± 2,300 | 580 ± 400 | 6.9 ± 0.01 | 22.0 ± 7.0 |
| YR | >1000 | 90 ± 20 | 45 ± 30 | 18.0 ± 6.0 | 3.3 ± 0.14 |
| Okadaic acid | 7.8 ± 1.5 | 2.2 ± 0.6 | 3.0 ± 1.2 | 90 ± 17 | 0.40 ± 0.18 |

In Table 2, growth inhibition was determined in plasmid transfected HeLa cells. Cells were seeded into 96 wells plates 24 hours following transfection with control plasmid (pIRESneo2), OATP1B1 or OATP1B3 containing vectors and 24 hours later exposed to a range of microcystin concentrations for a further 72 hours. Growth inhibition was determined using the SRB dye assay as described in the Materials and Methods. The $IC_{50}$ data presented in the table represent the concentration at which the absorbance is 50% of the untreated control wells, the $IC_{50}$ was determined by non-linear regression (variable slope) analysis using the GRAPHPAD PRISM® software. Phosphatase enzyme inhibition was determined using purified PP1 and PP2A enzyme. Enzyme was incubated with the microcystins at a range of concentrations for 10 minutes prior to the addition of [$^{33}$P]-ATP labeled Myelin Basic Protein. The de-phosphorylation reaction was allowed to proceed for 10 minutes, after which the reaction was stopped with TCA and released [$^{33}$P] was determined by liquid scintillation counting as described in the Material and Methods. The $IC_{50}$ was determined by non-linear regression (variable slope) analysis using the GRAPHPAD PRISM® software and represents the concentration at which the release of [$^{33}$P] was inhibited by 50% compared to the untreated enzyme control reaction. All data are presented as the mean±SD. of ≥3 replicate experiments.

Example 4

Microcystins Demonstrate Both Potent and Differential Inhibition of Protein Phosphatases The in vitro analysis of microcystin inhibition on purified PP1 and PP2A phosphatases is also shown in Table 2. The values determined are consistent with previously reported Ki values for microcystin LR and okadaic acid. The reported Ki values for microcystin-LR against PP1 and PP2A are 0.06-6 nM and <0.01-2 nM, respectively (17). Okadaic acid has a reported $IC_{50}$ of 60-500 nM for PP1 and 15-70 nM for PP2A (18).

HeLa cells is related more to PP2A inhibition than PP1 (FIG. 4B). Similar results were found in the HeLa cells transfected with OATP1B3 (data not shown). The relation between cytotoxicity and PP2A inhibition is further supported by the observation that the $IC_{50}$s of the analogs for growth inhibition and PP2A enzyme inhibition are both in the same sub-nanomolar range. The results with okadaic acid (closed square) further support this conclusion.

We measured global phosphatase inhibition in the transfected HeLa cells exposed to approximately equitoxic ($IC_{90}$) concentrations of microcystins to further examine the relationship between the cytotoxic effects and protein phosphatase inhibition. In these studies, OATP1B3-transfected HeLa cells and empty vector control cells were exposed for 6 hours to the microcystins at approximately equitoxic concentrations, and phosphatase activity in the cellular cytosol was then measured. As can be seen in FIG. 4C, total phosphatase inhibition does not directly correspond to cytotoxicity. For example, at a dose of approximately 2-fold greater than the cytotoxic $IC_{50}$ in OATP1B3-transfected HeLa cells, microcystin LF and LW (1 nM) had no discernable effect on total phosphatase activity. At a similar equitoxic dose, microcystin LR (10 nM) decreased total phosphatase activity by approximately 30% in OATP1B1-transfected cells. However, microcystin RR (1 µM) decreased total phosphatase activity by 90%. These results suggest that specific phosphatase inhibition, not global inhibition, is related to cytotoxicity. These results also suggest that at higher concentrations, microcystins may have inhibitory effects on other phosphatases.

Example 5

Cell Death Induced by Microcystin LR is Rapid

Figure 5:
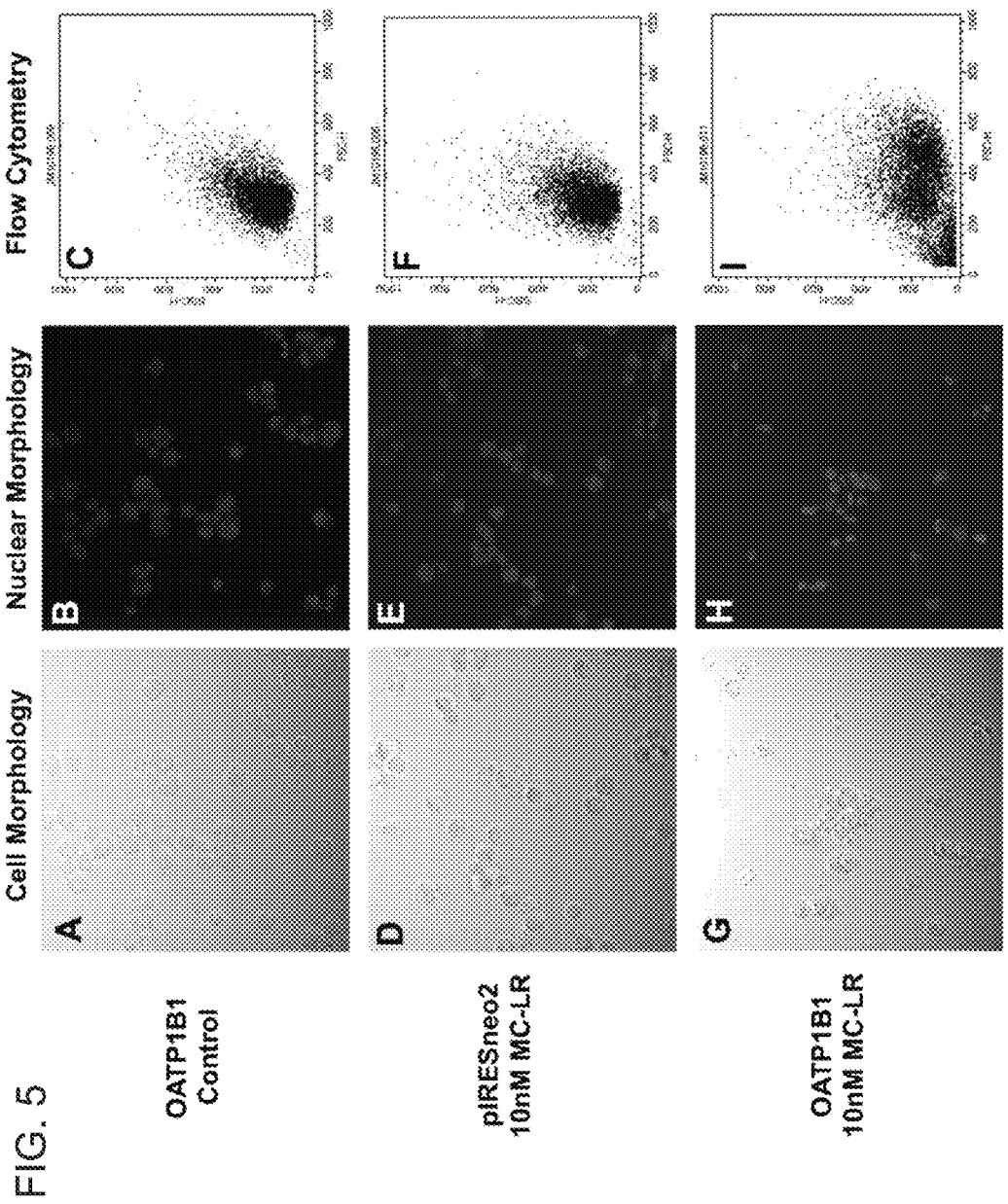
FIGS. 5A-5I. Cell death induced by 10 nM microcystin LR (MC-LR) 6 hours after treatment. Untreated OATP1B1 transfected HeLa cells (Panels A, B and C), 10 nM treated vector control (pIRESneo2) transfected HeLa cells (Panels D, E and F), and 10 nM treated OATP1B1 transfected HeLa cells (Panels G, H and I). Brightfield images used to visualize cellular morphology (Panels A, D and G). Fluorescent images showing Hoechst 33258 stain to visualize nuclear morphology and DNA condensation (Panels B, E and H), Flow cytometry plots of Side scatter (SSC) versus Forward scatter (FSC) displaying the changes in cell size and the formation of cell fragments (Panels C, F and I).
Figure 6:
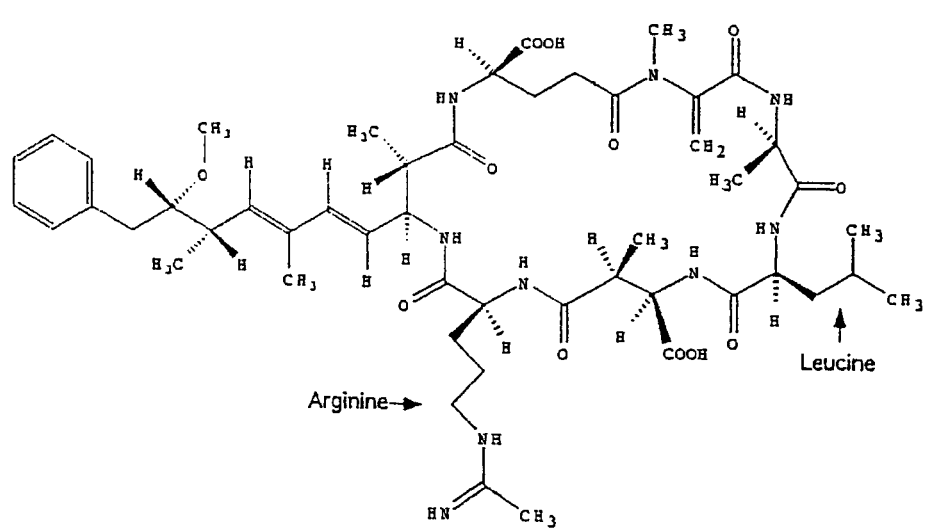
FIG. 6. The structure of microcystin LR. The positions of the two variable amino acids leucine (L) and arginine (R) that are specific for microcystin LR are shown.

FIG. 5 displays the results of microcystin LR induced cell death after a 6 hour exposure. Using confocal microscopy and changes in cell morphology shown by flow cytometry we have identified that exposure to Microcystin LR induced rapid changes in cell and nuclear morphology. Initial morphologic changes are rapid detachment from the culture surface, which occurs within the first hour of exposure (data not shown). By 6 hours microcystin LR-treated OATP1B1 expressing cells, display membrane blebbing (FIG. 5G), and massive cellular fragmentation can be detected using flow cytometry (FIG. 5I). Using Hoechst 33258 DNA stain, we also identified extensive chromatin condensation and fragmentation (FIG. 5H) following a 6 hour microcystin LR exposure. Control (pIRESneo2) transfectants similarly treated with 10 nM microcystin LR showed no changes in cellular morphology (FIGS. 5D and F) and nuclear condensation (FIG. 5E), comparable to the untreated OATP1B1-transfected control (FIGS. 5A, B and C), further supporting the evidence that microcystins require a transport mechanism for cellular uptake and toxicity. Taken together, these data demonstrate that once microcystin LR gains entry into cells it acts rapidly causing morphological changes which are indicative of cell death.

Example 6

Xenograft Model

Figure 7:
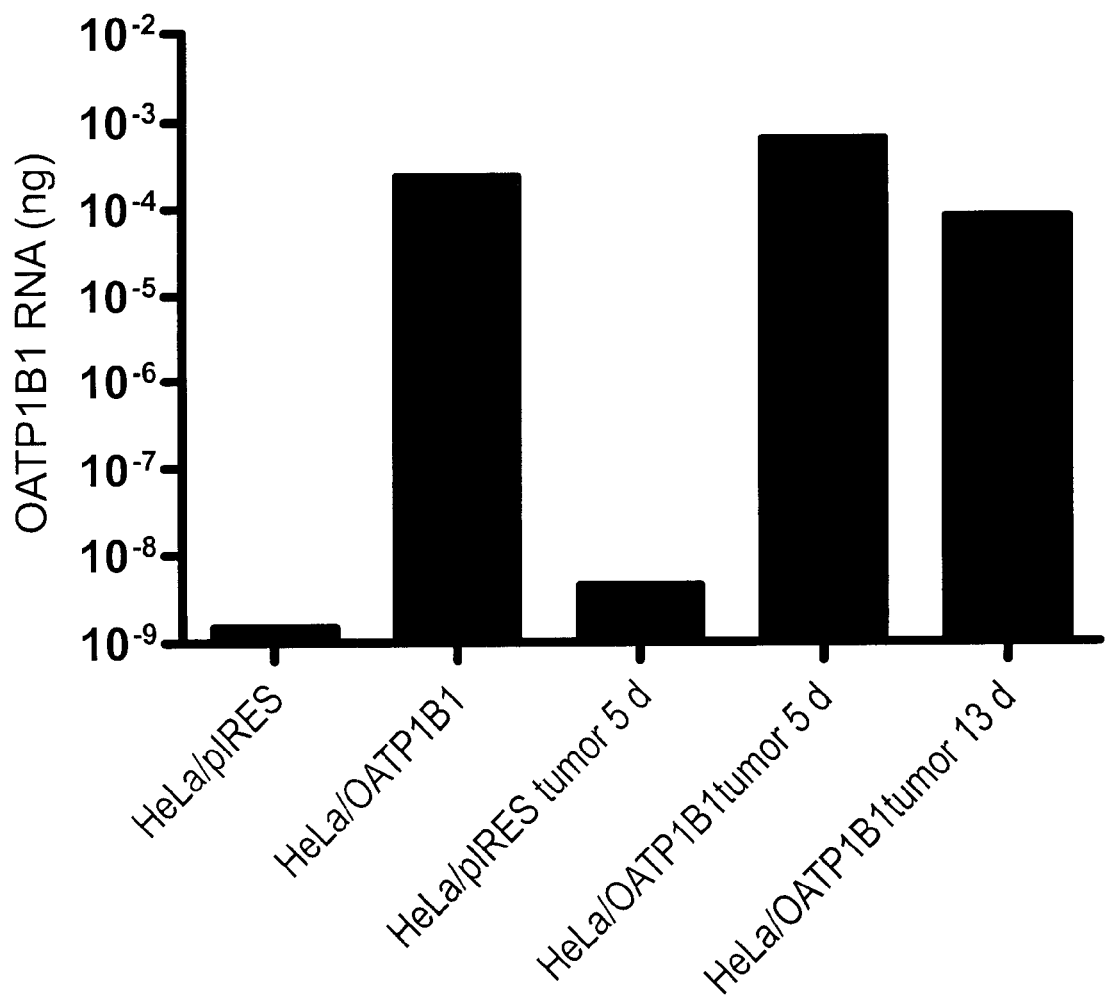
FIG. 7. OATP1B1 RNA levels determined using quantitative reverse transcription polymerase chain reaction (RT PCR) and normalized to the expression of β-actin. OATP1B1 levels were analyzed in the in the stable in vitro HeLa cell lines and tumor masses excised from untreated athymic nude mice 5 and 13 days after implantation. HeLa/pIRES is a control cell line that contains an empty expression vector. Expression levels in the OATP1B1 tumors are comparable with the levels seen in the OATP1B1 cell line.
Figure 8:
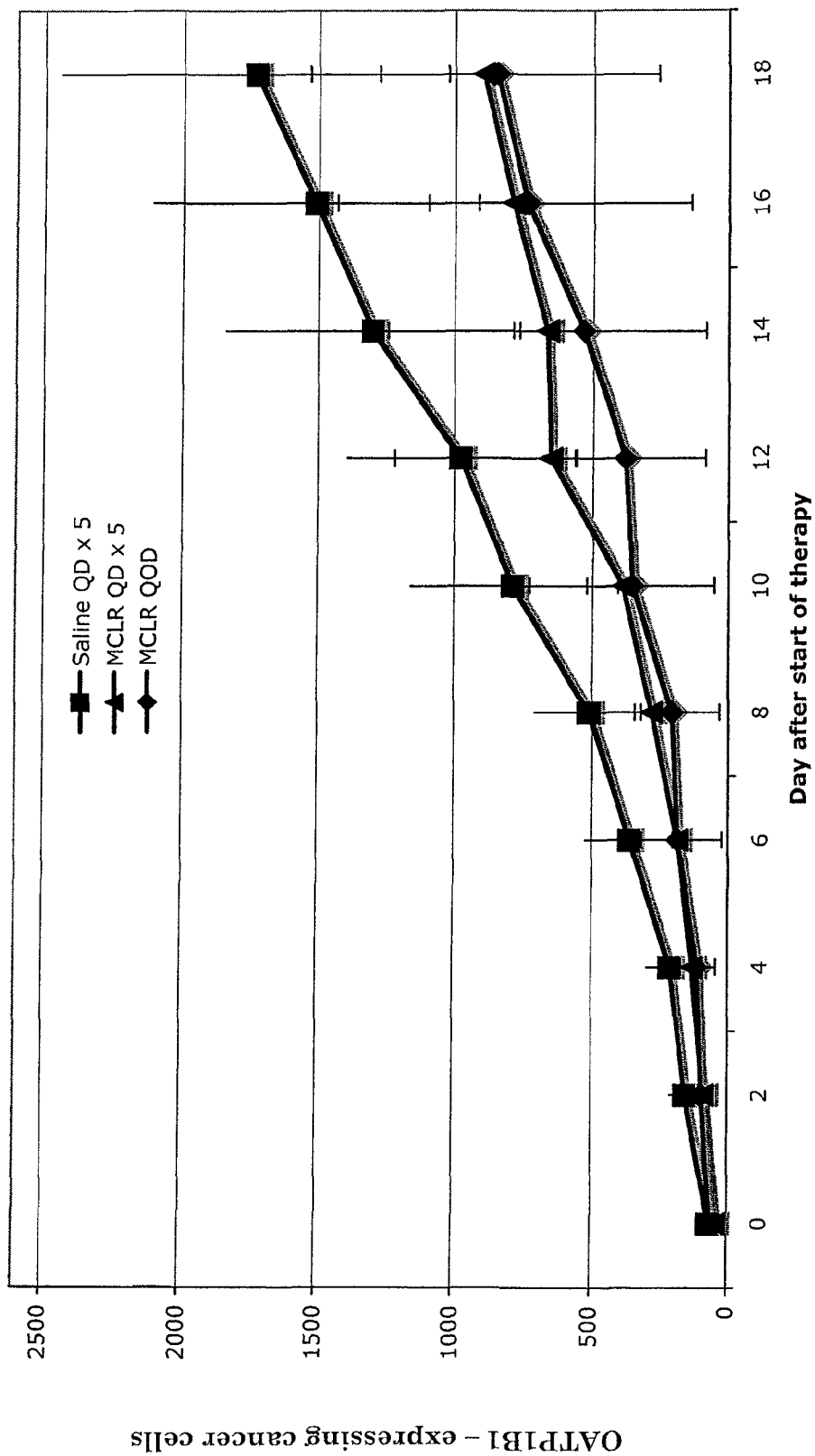
FIG. 8. OATP1B1-expressing cancer cells were injected into the flanks of athymic nude mice. After palpable tumors were formed, cohorts were either injected with saline 5 days per week with saline (controls, 'saline QD×5', squares); injected with microcystin LR 25 μg/kg 5 days per week (MCLR QD×5, triangles); or injected with microcystin LR 35 μg/kg every other day (MCLR QOD, diamonds). Tumors were measured every two days. The results represent the average±SD of cohorts of 3 or 4 mice.

Clones of HeLa cells that stably express both OATP1B3 and OATP1B1 have been isolated, and a preliminary study a preliminary study with stable OATP1B1-expressing HeLa cells transplanted into athymic nude mice has been conducted. The OATP1B1 gene was chosen for initial studies of hepatocellular carcinoma, a malignancy where OATP1B1 is expressed. Our in vitro data indicates that both OATP1B1 and OATP1B3 effectively mediate the uptake of microcystins, and can be expected to have similar function in vivo. We have also demonstrated that this cell line can grow in vivo and that the gene expression is maintained when grown as tumor xenografts (FIG. 7).

Example 7

OATP1B1-Expressing HeLa Xenografts Treated with Microcystin LR

Figure 3:
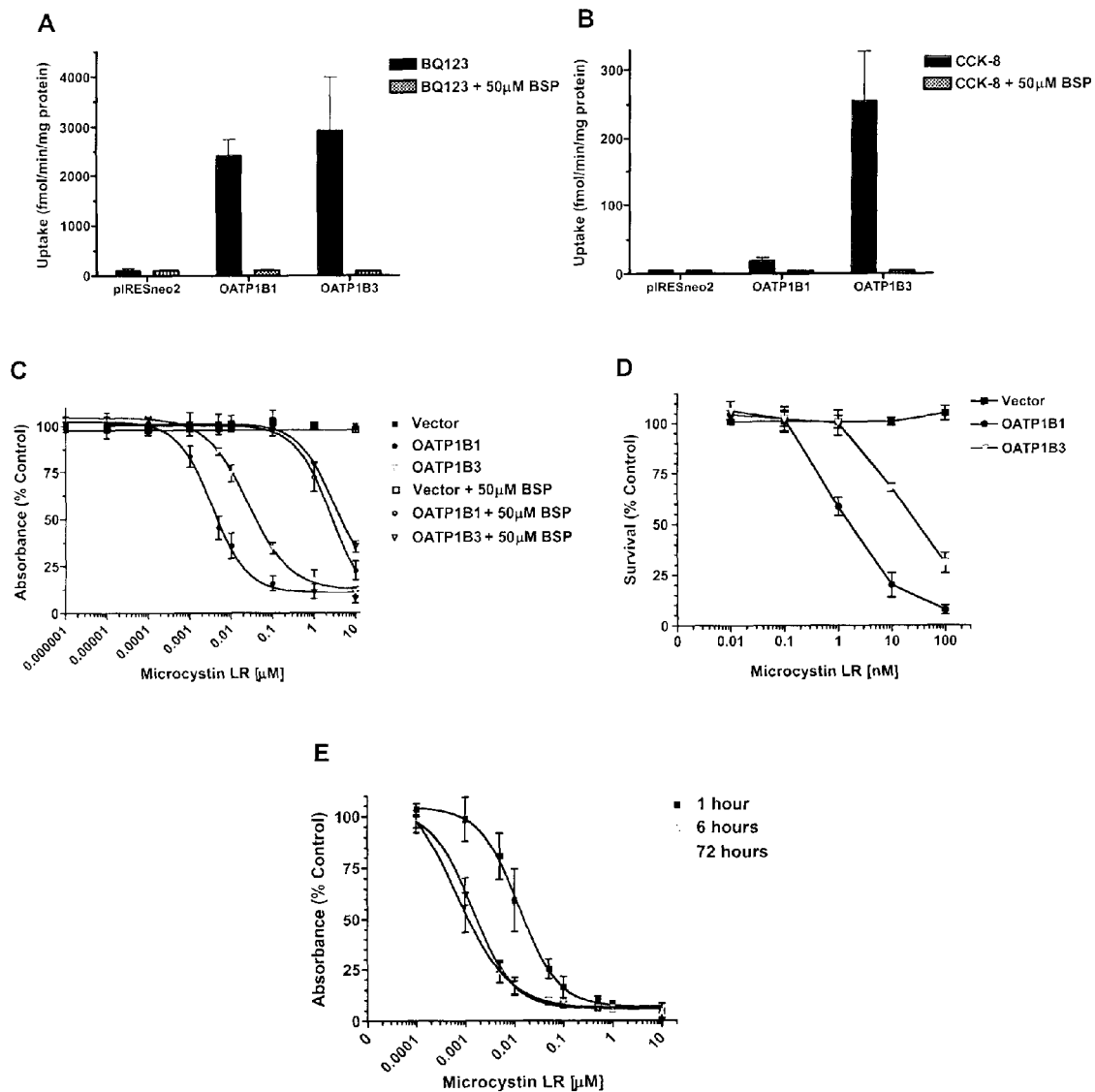
FIGS. 3A-3D. Uptake of radiolabeled OATP1B1 and OATP1B3 substrates. Cells were seeded in 6 well plates, transfected and assayed for uptake 48 hours later as described in the Material and Methods. A. [$^3$H]-BQ123 (0.5 μM for 30 minutes), a substrate of both OATP1B1 and OATP1B3 and B. [$^3$H]-CCK8 (5 nM for 10 minutes), a substrate specific for OATP1B3, both substrates were also co-incubated in the presence of the competitive substrate BSP (50 μM). The data shown are the mean±SD of 3 replicate experiments. (C) Growth inhibition of OATP1B1 (circles) and OATP1B3-transfected HeLa cells (triangles), and mock-transfected HeLa cells (squares) exposed to microcystin LR in the presence (open symbols) and absence (filled symbols) of the uptake inhibitor BSP. The cells were seeded in 96 wells plates 24 hours following transfection with either the control plasmid pIRESneo2, OATP1B1 or OATP1B3 containing vectors. Twenty-four hours after seeding, the cells were exposed to a range of microcystin LR concentrations for 72 hours with or without the competitive transport substrate BSP (50 μM). Growth inhibition was determined using the SRB dye assay as described in the Materials and Methods and data are presented as the percent of untreated control growth. The data shown are the mean±SD. of 3 replicate experiments. (D) Clonogenic survival of HeLa cells transfected with pIRESneo2 (■), OATP1B1 (●) or OATP1B3 (▼) following a 72 hour exposure to microcystin LR. The data shown are the mean±SD. of 3 replicate experiments. (E) Growth inhibition of OATP1B1-transfected HeLa cells exposed to microcystin LR for 1 (■), 6 (▲) and 72 (▼) hours. Growth inhibition was determined using the SRB dye assay and data are presented as the percent of untreated control growth. The data shown are the mean±SD. of 3 replicate experiments.

In this in vivo experiment of microcystin LR treatment, OATP1B1-expressing cancer cells were implanted subcutaneously in the flanks of 10 athymic nude mice and microcystin LR was administered in two schedules by intraperitoneal (IP) injection after tumors were established (FIG. 8). A cohort of 3 mice were injected with 35 μg/kg IP every other day and a second cohort of 3 mice received daily injections of 25 μg/kg Monday through Friday. A cohort of 4 mice served as controls and were injected IP with saline. The doses and schedules were all the first approximations, and other microcystin analogs are more potent in vitro. The graph shown in FIG. 8 shows the result of this first experiment, and demonstrates the proof-of-principle that established OATP1B1-expressing tumors respond to microcystin treatment. The therapy was tolerated; all mice survived the treatment regimens. The weight in the control group was 22.7±1.3 grams at day 0 and 26.1±2.0 grams at day 18; in the microcystin LR cohort treated daily the weight was 22.8±2.7 grams on day 0 and 19.0±1.2 grams on day 18; and in the cohort treated every other day, the weights were 21.6±0.8 grams on day 0 and 22.3±2.4 grams on day 18. The average tumor volume of the cohort treated every other day was 49% of control on day 18.

Discussion

The observation that microcystin LR and its analogs show potent growth inhibitory and cytoxicity activity in OATP1B1- and OATP1B3-transfected cells in comparison to control cells indicates both that the expression of these genes can impart selective sensitivity of cancer cells to cytotoxic substrates, and that phosphatase inhibition may be a valid target for anticancer drug development. Furthermore, the lack of activity of microcystin LR in the control HeLa cells demonstrates that the stumbling block for developing microcystins as anticancer agents may be that these phosphatase inhibitors have difficulty gaining intracellular access in standard in vitro cytotoxicity models. This potential difficulty is supported by both our observations and those of others, that even hepatic-derived cell lines do not reflect the level of transporter gene expression observed in the tissue and tumors of origin. In the case of OATP1B1 we found no detectable expression in any of the HCC or immortalized hepatocyte cell lines. In the case of OATP1B3, the level of mRNA expression in HCC and hepatocyte cell lines was at the limit of detection, and orders of magnitude lower than the expression levels seen in normal adult liver. In particular, the widely used Hep3B cell line does not express OATP1B1 and the level of OATP1B3 is orders of magnitude lower than the levels measured in normal liver. Also, another widely used model of hepatocellular carcinoma, the HepG2 cell line, also does not express either transporter (7). Similarly, the level of RNA expression in lung cancer cell lines is also low, even though direct measurement of RNA levels in lung tumor tissue showed increased expression relative to normal lung tissue, with the increased expression in the tumor samples being comparable to that of a normal liver reference. In the case of both transporters, the constitutive levels in all of the hepatic cell lines was at the level of the untransfected HeLa cells, whereas the transfected HeLa cells had mRNA levels similar to the levels measured in normal liver. We have seen a similar down regulation in cell lines versus tumors in the case of another membrane transporter, OCT6 (19). Supporting our observations, the loss of microcystin sensitivity in freshly isolated trout and murine hepatocytes was observed to coincide with the rapid loss of OATP transporter gene expression when the hepatocytes are maintained in cell culture (20). Thus, down-regulation of membrane transport that occurs in adaptation to in vitro growth conditions has the potential to limit the interpretation of cell culture-based screening systems for polar cytotoxins that depend on specific mechanisms of drug uptake.

Since transporter gene expression in tumors cannot be extrapolated from cell lines, direct measurement of tumor gene expression is required. However, studies quantifying mRNA levels in tumors also have limitations in interpretation. It is important to acknowledge that, while the data demonstrate increased expression of OATP1B3 mRNA in lung tumors, these data must be interpreted with caution, as the mRNA levels do not necessarily reflect either protein expression or function. The actual sensitivity of NSCLC tumors to microcystin analogs, and of microcystin uptake in NSCLC tumors relative to hepatocytes, are important questions to be explored with xenograft models (see, e.g., Examples 6 and 7 herein).

The microcystin concentrations that produced cytotoxicity in the transfected HeLa cells in our study, in the sub-nanolar range for microcystin LF and microcystin LW, appear to be significantly less than the doses required for hepatic toxicity. In mice given a sub-lethal dose of microcystin LR (35 μg/kg), the peak plasma concentration achieved was 428 nM (21), compared to the $IC_{50}$s of 5 nM and 39 nM for microcystin LR in OATP1B1 and OATP1B3-transfected HeLa cells, respectively (Table 2). Also, microcystin rapidly accumulate in the liver, with 70% of the total dose accumulating in the liver by 30 min after the injection (21). We have demonstrated that the cytotoxic activity of microcystin LR is rapid, and although maximal activity was not seen until 6 hours, a 1 hour exposure demonstrated significant levels of activity (FIG. 3E).

Our data strongly suggest that microcystin cytotoxicity in HeLa cells is related to specific PP2A inhibition. We found no correlation between global phosphatase inhibition and cytotoxicity. The similar concentrations for PP2A enzyme inhibition and growth inhibition, and the linear correlation between the growth $IC_{50}$ and the enzyme $IC_{50}$ for microcystin analogs, both suggest that specific PP2A inhibition is related to the toxic effect.

The high concentration of microcystin in the liver achieved with a sublethal dose (21) suggests that hepatocytes may differ from cancer cells in the mechanism of microcystin toxicity. First, hepatic lethality may be related to an intracellular target other than PP2A. One such target may be aldehyde dehydrogenase 11, an enzyme involved in acetetaldehyde detoxification and prevention of free radical formation, which was recently identified as a microcystin target from a peptide fragment that physically associated with microcystin LR using phage display methodology (22). Another potential microcystin target is the β subunit of ATP-synthase, which was shown to be a microcystin-binding protein using an anti-microcystin antibody affinity purification column (23).

Second, reports of microcystin cytotoxicity in non malignant cells, in which a significantly higher dose is required for toxicity, is seemingly related to formation of reactive oxygen species (24) and resultant DNA damage (25). In lymphocytes in vitro, the mechanism of microcystin toxicity was associated with free radical formation; in those studies cells were exposed to micromolar concentrations of microcystin LR (26, 27), in comparison to the sub-nanomolar range in the transfected HeLa cells.

Third, phosphatase inhibition may have different effects in tumor cells versus normal cells. Although protein phosphatases have tumor suppressor properties, phosphatases have been also been reported to promote cell growth and survival (9, 10). The cytotoxic effect of phosphatase inhibition may depend upon the reliance of a particular cell on the activity of specific kinases, which are often abnormally regulated in cancer. For example, the phosphatase inhibitor okadaic acid has been shown to induce apoptosis in a variety of cell lines, with increased sensitivity reported in cells carrying mutated Ras (28). Okadaic acid also induced apoptosis in malignant glioma cells, in studies which suggested an integral role for ERK and JNK kinases in promoting cell death (29). Rapid apoptosis has also been seen in primary hepatocytes following microinjection with both microcystin LR and nodularin, characterised by cytoplasmic shrinkage, chromatin condensation, membrane blebbing and procaspase 3 cleavage (30). Similarly, we have identified rapid cell death (within 6 hours), although at a much lower concentration (10 nM) than those used by Fladmark and colleagues (nodularin>250 μM and microcystin LR>50 μM).

Finally, in addition to potential differences in microcystin intracellular targets between hepatocytes and cancer cells, there are also numerous metabolic differences between the normal hepatocyte and the malignant cell, and these differences might be exploited to create a therapeutic window for microcystin toxins. Microcystin and the related toxic cyclic peptide nodularin appear to stimulate glutathione-dependent detoxification pathways in hepatocytes. Exposure of rat hepatocytes to sub-lethal concentrations of microcystin LR results in an acute increase in intracellular glutathione and an increase in the formation of reactive oxygen species (31). Significantly, addition of N-acetylcysteine (NAC) to the culture medium, an agent that increases intracellular glutathione concentrations, decreased sensitivity of cultured rat hepatocytes to microcystic cyanobacteria extracts. Conversely, buthionine sulfoximine (BSO), an agent that decreases intracellular glutathione, increased the sensitivity of the cultured hepatocytes to the cyanobacteria extract (32). These studies suggest that glutathione may play a role in the in vivo hepatic detoxification of microcystins at high concentrations. In our HeLa cell model, neither NAC nor BSO affected microcystin toxicity (data not shown).

In conclusion, therapeutic microcystin analogs may have the potential to exploit both differences in the mechanisms of toxicity and the availability of detoxification mechanisms in tumors versus normal hepatic tissue. The restricted hepatic expression of OATP1B1 and OATP1B3 would help to prevent toxicities to non-malignant tissues other than liver, and the expression of these transporters in NSCLC and hepatocellular carcinoma suggests that these tumors could be targeted with transporter-specific cytotoxins. Microcystins, as stable cyclic peptides with two variable amino acid positions, are attractive candidates for combinatorial synthesis, and the variation in potency between the first 5 microcystin analogs tested suggests that other analogs may be even more potent.

While the present invention has been described with reference to specific embodiments, this application is intended to cover those various changes and substitutions that may be made by those of ordinary skill in the art without departing from the spirit and scope of the appended claims.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

All publications cited herein are hereby incorporated by reference in their entirety.

REFERENCES

1. Taylor W P, Widlanski T S. Charged with meaning: the structure and mechanism of phosphoprotein phosphatases. Chem Biol 1995; 2:713-8.
2. Cheng A, Dean N M, Honkanen R E. Serine/threonine protein phosphatase type 1gamma1 is required for the completion of cytokinesis in human A549 lung carcinoma cells. J Biol Chem 2000; 275:1846-54.
3. MacKintosh C, Beattie K A, Klumpp S, Cohen P, Codd G A. Cyanobacterial microcystin-LR is a potent and specific inhibitor of protein phosphatases 1 and 2A from both mammals and higher plants. FEBS Lett 1990; 264:187-92.
4. WHO. Cyanobacterial toxins: microcystin-LR. Guidelines for Drinking-Water Quality, World Health Organization. Geneva: World Health Organization; 1998. p. 95-110.
5. Cui Y, Konig J, Nies A T, et al. Detection of the human organic anion transporters SLC21A6 (OATP2) and SLC21A8 (OATP8) in liver and hepatocellular carcinoma. Lab Invest 2003; 83:527-38.
6. Hagenbuch B, Meier P J. Organic anion transporting polypeptides of the OATP/SLC21 family: phylogenetic classification as OATP/SLCO superfamily, new nomenclature and molecular/functional properties. Pflugers Arch 2003; 1-8.
7. Abe T, Unno M, Onogawa T, et al. LST-2, a human liver-specific organic anion transporter, determines methotrexate sensitivity in gastrointestinal cancers. Gastroenterology 2001; 120:1689-99.

8. Janssens V, Goris J. Protein phosphatase 2A: a highly regulated family of serine/threonine phosphatases implicated in cell growth and signalling. Biochem J 2001; 353:417-39.
9. Janssens V, Goris J, Van Hoof C. PP2A: the expected tumor suppressor. Curr Opin Genet Dev 2005; 15:34-41.
10. Millward T A, Zolnierowicz S, Hemmings B A. Regulation of protein kinase cascades by protein phosphatase 2A. Trends Biochem Sci 1999; 24:186-91.
11. Messner D J, Romeo C, Boynton A, Rossie S. Inhibition of PP2A, but not PP5, mediates p53 activation by low levels of okadaic acid in rat liver epithelial cells. J Cell Biochem 2006;
12. Yan Y, Shay J W, Wright W E, Mumby M C. Inhibition of protein phosphatase activity induces p53-dependent apoptosis in the absence of p53 transactivation. J Biol Chem 1997; 272:15220-6.
13. Lin S S, Bassik M C, Suh H, et al. PP2A regulates BCL-2 phosphorylation and proteasome-mediated degradation at the endoplasmic reticulum. J Biol Chem 2006;
14. Hagenbuch B, Meier P J. The superfamily of organic anion transporting polypeptides. Biochim Biophys Acta 2003; 1609:1-18.
15. Skehan P, Storeng R, Scudiero D, et al. New colorimetric cytotoxicity assay for anticancer drug screening. J Natl Cancer Inst 1990; 82:1107-112.
16. Liu S, Stromberg A, Tai H H, Moscow J A. Thiamine transporter gene expression and exogenous thiamine modulate the expression of genes involved in drug and prostaglandin metabolism in breast cancer cells. Mol Cancer Res 2004; 2:477-87.
17. Fujiki H, Suganuma M. Tumor promotion by inhibitors of protein phosphatases 1 and 2A: the okadaic acid class of compounds. Adv Cancer Res 1993; 61:143-94.
18. Ishihara H, Martin B L, Brautigan D L, et al. Calyculin A and okadaic acid: inhibitors of protein phosphatase activity. Biochem Biophys Res Commun 1989; 159:871-7.
19. Gong S, Lu X, Xu Y, Swiderski C F, Jordan C T, Moscow J A. Identification of OCT6 as a novel organic cation transporter preferentially expressed in hematopoietic cells and leukemias. Exp Hematol 2002; 30:1162-9.
20. Boaru D A, Dragos N, Schirmer K. Microcystin-LR induced cellular effects in mammalian and fish primary hepatocyte cultures and cell lines: a comparative study. Toxicology 2006; 218:134-48.
21. Robinson N A, Pace J G, Matson C F, Miura G A, Lawrence W B. Tissue distribution, excretion and hepatic biotransformation of microcystin-LR in mice. J Pharmacol Exp Ther 1991; 256:176-82.
22. Chen T, Cui J, Liang Y, et al. Identification of human liver mitochondrial aldehyde dehydrogenase as a potential target for microcystin-LR. Toxicology 2006; 220:71-80.
23. Mikhailov A, Harmala-Brasken A S, Hellman J, Meriluoto J, Eriksson J E. Identification of ATP-synthase as a novel intracellular target for microcystin-LR. Chem Biol Interact 2003; 142:223-37.
24. Ding W X, Nam Ong C. Role of oxidative stress and mitochondrial changes in cyanobacteria-induced apoptosis and hepatotoxicity. FEMS Microbiol Lett 2003; 220:1-7.
25. Ding W X, Shen H M, Zhu H G, Lee B L, Ong C N. Genotoxicity of microcystic cyanobacteria extract of a water source in China. Mutat Res 1999; 442:69-77.
26. Lankoff A, Carmichael W W, Grasman K A, Yuan M. The uptake kinetics and immunotoxic effects of microcystin-LR in human and chicken peripheral blood lymphocytes in vitro. Toxicology 2004; 204:23-40.
27. Lankoff A, Krzowski L, Glab J, et al. DNA damage and repair in human peripheral blood lymphocytes following treatment with microcystin-LR. Mutat Res 2004; 559:131-42.
28. Rajesh D, Schell K, Verma A K. Ras mutation, irrespective of cell type and p53 status, determines a cell's destiny to undergo apoptosis by okadaic acid, an inhibitor of protein phosphatase 1 and 2A. Mol Pharmacol 1999; 56:515-25.
29. Rami B G, Chin L S, Lazio B E, Singh S K. Okadaic-acid-induced apoptosis in malignant glioma cells. Neurosurg Focus 2003; 14:e4.
30. Fladmark K E, Brustugun O T, Hovland R, et al. Ultrarapid caspase-3 dependent apoptosis induction by serine/threonine phosphatase inhibitors. Cell Death Differ 1999; 6:1099-108.
31. Bouaicha N, Maatouk I. Microcystin-LR and nodularin induce intracellular glutathione alteration, reactive oxygen species production and lipid peroxidation in primary cultured rat hepatocytes. Toxicol Lett 2004; 148:53-63.
32. Ding W X, Shen H M, Ong C N. Microcystic cyanobacteria extract induces cytoskeletal disruption and intracellular glutathione alteration in hepatocytes. Environ Health Perspect 2000; 108:605-9.

What is claimed is:

1. A method of treating cancer, said method comprising administering to a mammalian subject in need thereof a pharmaceutically effective amount of a microcystin which is not microcystin LR, wherein the cancer comprises cancer cells that express at least one of OATP1B1 and OATP1B3 and the microcystin has improved cytotoxicity for the cells expressing at least one of OATP1B1 and OATP1B3 as compared to microcystin LR, wherein the cancer is selected from the group consisting of gastrointestinal cancer, lung cancer, gastric cancer, colon cancer, pancreatic cancer, gall bladder cancer, breast cancer and glioblastoma; wherein said microcystin has the following formula:
cyclo (D-Ala-X-erythro-β-methyl-D-iso-Asp-Y-adda-D-iso-Glu-N-methyldehydro-Ala) wherein X is leucine and Y is phenylalanine (MCLF) or tryptophan (MCLW).

2. The method of claim 1, wherein said microcystins are substrates of at least one of OATP1B1 and OATP1B3.

3. The method of claim 2, wherein said microcystins are substrates of both OATP1B1 and OATP1B3.

4. The method of claim 2, wherein said microcystins are substrates of OATP1B3 and not OATP1B1.

5. The method of claim 2, wherein said microcystins are substrates of OATP1B1 and not OATP1B3.

6. The method of claim 1, wherein said microcystin has at least one of improved cytotoxic potency and improved cytotoxic selectivity as compared to microcystin LR.

7. The method of claim 1, wherein said microcystin is naturally-occurring.

8. The method of claim 1, wherein said microcystin is synthetic.

9. The method of claim 1, wherein said cancer comprises cells that express both OATP1B1 and OATP1B3.

10. The method of claim 1, wherein said cancer comprises cells that express OATP1B3 and not OATP1B1.

11. The method of claim 1, wherein said cancer comprises cells that express OATP1B1 and not OATP1B3.

12. The method of claim 1, wherein said microcystin is administered at a dose that does not result in hepatic cytotoxicity.

13. The method of claim 1, wherein said microcystin is administered as a pharmaceutical composition comprising one or more of a pharmaceutically acceptable diluent, carrier, and excipient.

14. The method of claim 1, wherein said microcystin is administered in combination with other cancer modalities.

15. The method of claim 14, wherein said other cancer modalities are selected from the group consisting of: chemotherapy, surgery, radiotherapy, hyperthermia, immunotherapy, hormone therapy, biologic therapy, and drugs to ameliorate the adverse side effects of said cancer modalities.

16. The method of claim 1, wherein said cancer is non-small cell lung cancer, and said microcystin is selected from the group consisting of: cyclo (D-Ala-Leu-erythro-β-methyl-D-iso-Asp-Phe-Adda-D-iso-Glu-N-methyldehydro-Ala) and cyclo (D-Ala-Leu-erythro-β-methyl-D-iso-Asp-Try-Adda-D-iso-Glu-N-methyldehydro-Ala).

17. The method of claim 1, wherein said cancer is hepatocellular carcinoma, and said microcystin is selected from the group consisting of: cyclo (D-Ala-Leu-erythro-β-methyl-D-iso-Asp-Phe-Adda-D-iso-Glu-N-methyldehydro-Ala) and cyclo (D-Ala-Leu-erythro-β-methyl-D-iso-Asp-Try-Adda-D-iso-Glu-N-methyldehydro-Ala).

18. The method of claim 1, wherein said cancer is colon cancer.

* * * * *